(12) United States Patent
Soyupak et al.

(10) Patent No.: US 7,838,240 B2
(45) Date of Patent: *Nov. 23, 2010

(54) MN/CA IX/CA9 AND RENAL CANCER PROGNOSIS

(75) Inventors: Bülent Soyupak, Adana (TR); Seyda Erdoğan, Adana (TR)

(73) Assignee: Institute of Virology of the Slovak Academy of Sciences, Bratislava (SK)

( * ) Notice: Subject to any disclaimer, the term of this patent is extended or adjusted under 35 U.S.C. 154(b) by 0 days.

This patent is subject to a terminal disclaimer.

(21) Appl. No.: 12/321,506

(22) Filed: Jan. 22, 2009

(65) Prior Publication Data

US 2009/0191557 A1  Jul. 30, 2009

Related U.S. Application Data

(63) Continuation of application No. 11/578,744, filed as application No. PCT/US2005/015587 on May 4, 2005, now Pat. No. 7,482,129.

(60) Provisional application No. 60/568,019, filed on May 4, 2004.

(51) Int. Cl.
*C12Q 1/68* (2006.01)
*G01N 33/53* (2006.01)

(52) U.S. Cl. .......................................... 435/6; 435/7.1

(58) Field of Classification Search ................. None
See application file for complete search history.

(56) References Cited

U.S. PATENT DOCUMENTS

| | | | | |
|---|---|---|---|---|
| 5,387,676 A | 2/1995 | Zavada et al. | ............... | 536/23.5 |
| 5,955,075 A | 9/1999 | Zavada et al. | ............ | 424/138.1 |
| 5,972,353 A | 10/1999 | Zavada et al. | ............ | 424/277.1 |
| 6,004,535 A | 12/1999 | Zavada et al. | ............... | 424/9.34 |
| 7,482,129 B2 * | 1/2009 | Soyupak et al. | ............... | 435/7.1 |
| 2005/0158809 A1 | 7/2005 | Bui et al. | .................... | 435/7.23 |

FOREIGN PATENT DOCUMENTS

| | | |
|---|---|---|
| WO | WO 93/18152 | 9/1993 |
| WO | WO 95/34650 | 12/1995 |
| WO | WO 00/24913 | 5/2000 |
| WO | WO 03/089659 | 10/2003 |
| WO | WO 03/100029 | 12/2003 |

OTHER PUBLICATIONS

Bui et al, Clin. Cancer Res. 9: 802 (2003).*
Brewer et al., "A Study of Biomarkers in Cervical Carcinoma and Clinical Correlation of the Novel Biomarker MN," *Gynecologic Oncology*, 63: 337-344 (1996).
Bui et al., "Carbonic Anhydrase IX Is an Independent Predictor of Survival in Advanced Renal Clear Cell Carcinoma: Implications for Prognosis and Therapy," *Clin. Cancer Res.*, 9(2): 802-811 (2003).
Bui et al., "Prognostic value of carbonic anhydrase IX and Ki67 as predictors of survival for renal clear cell carcinoma," *J. Urol.*, 171: 2461-2466 (2004).
Bui et al., "Prognostic factors and molecular markers for renal cell carcinoma," *Expert Rev. Anticancer Ther.*, 1(4): 565-575 (2001).
Chia et al., "Prognostic significance of a novel hypoxia-regulated marker, carbonic anhydrase IX, in invasive breast carcinoma," *J. Clin. Oncol.*, 19: 3660-3668 (2001).
Divgi et al., "Phase I/II radioimmunotherapy trial with iodine-131-labeled monoclonal antibody G250 in metastatic renal cell carcinoma," *Clin. Cancer Res.*, 4: 2729-2739 (1998).
Fuhrman et al., "Prognostic significance of morphologic parameters in renal cell carcinoma," *Am. J. Surg Pathol.*, 6: 655-663 (1982).
Giatromanolaki et al. "Expression of hypoxia-inducible carbonic anhydrase-9 relates to angiogenic pathways and independently to poor outcome in non-small cell lung cancer," *Cancer Res.*, 7992-7998 (2001).
Ivanov et al., "Down-regulation of transmembrane carbonic anhydrases in renal cell carcinoma cell lines by wild-type von Hippel-Lindau transgenes," *Proc. Natl. Acad. Sci.* (USA), 95: 12596-12601 (1998).
Ivanov et al., "Expression of hypoxia-inducible cell-surface transmembrane carbonic anhydrases in human cancer," *Am. J. Pathol.*, 158: 905-919 (2001).
Jocham et al, "Adjuvant autologous renal tumor cell vaccine and risk of tumour progression in patients with renal-cell carcinoma after radical nephrectomy: Phase III, randomized controlled trial," *Lancet*, 363: 594-599 (2004).
Kim et al., "Using protein expressions to predict survival in clear cell renal carcinoma," *Clin. Cancer Res.*, 10(16): 5464-5471 (2004).
Kim et al., "Using tumor markers to predict the survival of patients with metastatic renal cell carcinoma," *J. Urol.*, 173(5): 1496-1501 (2005).
Koukourakis et al., "Hypoxia-regulated carbonic anhydrase-9 (CA9) relates to poor vascularization and resistance of squamous cell head and neck cancer to chemoradiotherapy," *Clin. Cancer Res.*, 7: 3399-3403 (2001).

(Continued)

*Primary Examiner*—James Martinell
(74) *Attorney, Agent, or Firm*—Leona L. Lauder; Joan C. Harland; Barbara A. Shimei

(57) ABSTRACT

Herein disclosed are methods that are prognostic for renal cell carcinoma, particularly renal clear cell carcinoma, afflicting a vertebrate. An exemplary prognostic method comprises detecting the presence of, and quantitating the level and/or extent of a MN/CA9 gene expression product in a sample from the affected subject, wherein if 50% or fewer cells are found to express the MN/CA9 gene, then the subject is considered to have a poorer prognosis. MN/CA9 gene expression products useful in the prognostic methods include MN protein, MN polypeptide and/or MN nucleic acids. The methods are useful as an aid in the selection of treatment for a patient with renal cell carcinoma, alone or in combination with conventional tumor stage and/or grade information. The methods of the invention can be used, for example, to identify those patients requiring more aggressive therapy regimens, or those patients most likely to respond to adjuvant immunotherapies, particularly MN/CA IX/CA9-targeted therapies.

19 Claims, 3 Drawing Sheets

OTHER PUBLICATIONS

Liao and Stanbridge, "Expression of the MN Antigen in Cervical Papanicolaou Smears Is an Early Diagnostic Biomarker of Cervical Dysplasia," *Cancer Epidemiology, Biomarkers & Prevention*, 5: 549-557 (1996).

Liao et al., "Identification of the MN antigen as a diagnostic biomarker of cervical intraepithelial squamous and glandular neoplasia and cervical carcinomas," *Am. J. Pathol.*, 145: 598-609 (1994).

Liao et al., "Identification of the MN/CA9 protein as a reliable diagnostic biomarker of clear cell carcinoma of the kidney," *Cancer Res.*, 57: 2827-2831 (1997).

Loncaster et al., "Carbonic anhydrase (CA IX) expression, a potential new intrinsic marker of hypoxia: correlations with tumor oxygen measurements and prognosis in locally advanced carcinoma of the cervix," *Cancer Res.*, 61: 6394-6399 (2001).

McKiernan et al., "Expression of the Tumor-associated Gene *MN*: A Potential Biomarker for Human Renal Cell Carcinoma," *Cancer Res.*, 57: 2362-2365 (1997).

Murakami et al., "*MN/CA9* gene expression as a potential biomarker in renal cell carcinoma," *BJU Int.*, 83: 743-747 (1999).

Novick and Campbell, *Renal tumors*; in Walsh, P., editor, Campell's Urology, Philadelphia: Saunders, pp. 2672-2731 (2002).

Oosterijk et al., "Monoclonal antibody G250 recognizes a determinant present in renal cell carcinoma and absent from normal kidney," *Int. J. Cancer*, 38: 489-494 (1986).

Pastorek et al., "Cloning and characterization of MN, a human tumor-associated protein with a domain homologous to carbonic anhydrase and a putative helex-loop-helix DNA binding segment," *Oncogene*, 9: 2877-2888 (1994).

Pastorekova and Zavada, "Carbonic anhydrase IX (CA IX) as a potential target for cancer therapy," *Cancer Therapy*, 2: 245-262 (2004).

Pastorekova et al., "A novel quasi-viral agent, MaTu, is a two-component system," *Virology*, 187: 620-626 (1992).

Pastorekova et al., "Carbonic Anhydrase IX, MN/CA IX: Analysis of stomach complementary DNA sequence and expression in human and rat alimentary tracts," *Gastroenterology*, 112: 398-408 (1997).

Potter and Harris, "Diagnostic, prognostic and therapeutic implications of carbonic anhydrases in cancer," *Br. J. Cancer*, 89: 2-7 (2003).

Rioux-Leclercq et al., "Value of immunohistochemical Ki-67 and p53 determinations as predictive factors of outcome in renal cell carcinoma," *Urology*, 55(4): 501-505 (2000).

Saarino et al., "Immunohistochemical study of colorectal tumors for expression of a novel transmembrane carbonic anhydrase, MN/CA IX, with potential value as a marker of cell proliferation," *Am. J. Pathol.*, 153: 279-285 (1998).

Swinson et al., "Carbonic anhydrase IX expression, a novel surrogate marker of tumor hypoxia, is associated with a poor prognosis in non-small cell lung cancer," *J. Clin. Oncol.*, 21: 473-482 (2003).

Tso et al., "Induction of G250-targeted and T-cell mediated antitumor activity against renal cell carcinoma using a chimeric fusion protein consisting of G250 and granulocyte/monocyte-colony stimulating factor," *Cancer Res.*, 7925-7933 (2001).

Tsui et al., "Prognostic indicators for renal cell carcinoma: a multivariate analysis of 643 patients using the revised 1997 TNM staging criteria," *J. Urol.*, 163(4): 1090-1095 (2000).

Uemura et al., "Expression of Tumor-Associated Antigen MN/G250 in Urologic Carcinoma: Potential Therapeutic Target," *J. Urol.*, 157 (4 Suppl.): 377 (Abstract 1475; 1997).

Uemura et al., "MN/CA IX/G250 as a potential target for immunotherapy of renal cell carcinomas," *Br. J. Cancer*, 81: 741-746 (1999).

Wingo et al., "The catalytic properties of human carbonic anhydrase IX," *Biochem. Biophys. Res. Commun.*, 288: 666-669 (2001).

Wykoff et al. "Hypoxia-inducible expression of tumor-associated carbonic anhydrases," *Cancer Res.*, 60: 7075-7083 (2000).

Zavada et al., "Expression of MaTu-MN protein in human tumor cultures and in clinical specimens," *Int. J. Cancer*, 54: 268-274 (1993).

Zavada et al., "Soluble form of carbonic anhydrase IX (CA IX) in the serum and urine of renal carcinoma patients," *Br. J. Cancer*, 89: 1067-1071 (2003).

Guinan et al., "TNM Staging of Renal Cell Carcinoma." *Cancer*, 80: 992-993 (1997).

Tsui et al., "Prognostic Indicators for Renal Cell Carcinoma: A Multivariate Analysis of 643 Patients Using the Revised 1997 TNM Staging Criteria," *The Journal of Urology*, 168: 1090-1095 (Apr. 2000).

* cited by examiner

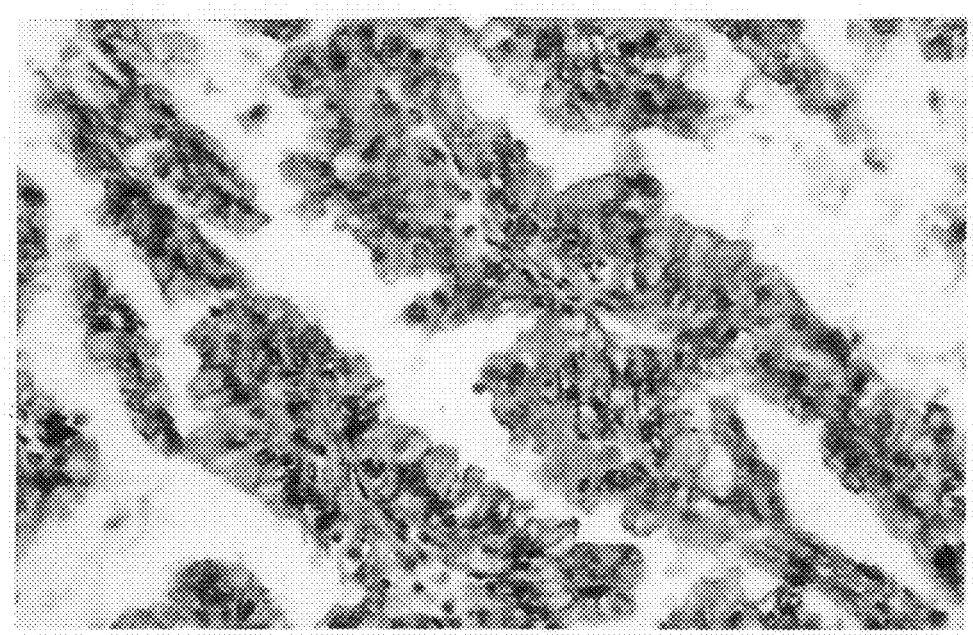
High pattern of staining seen in papillary carcinoma.
FIG._1
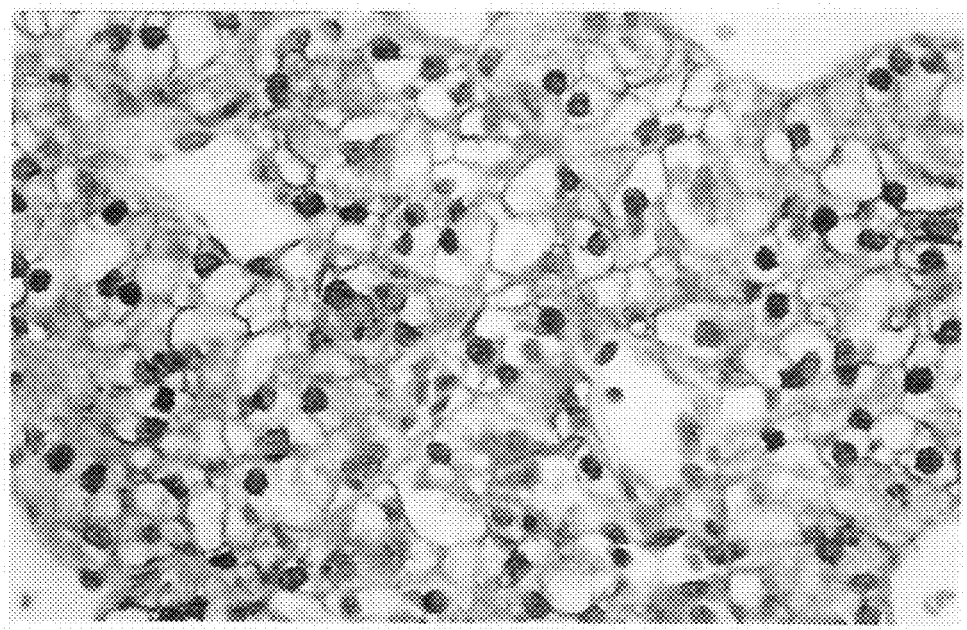
Intensive membraneous staining seen in clear cell carcinoma.
FIG._2

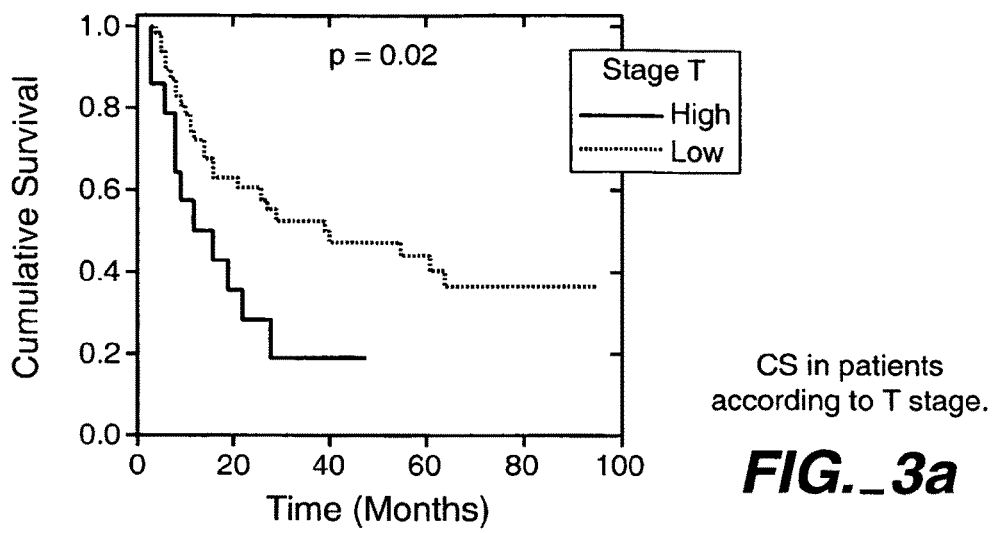
CS in patients according to T stage.
FIG._3a
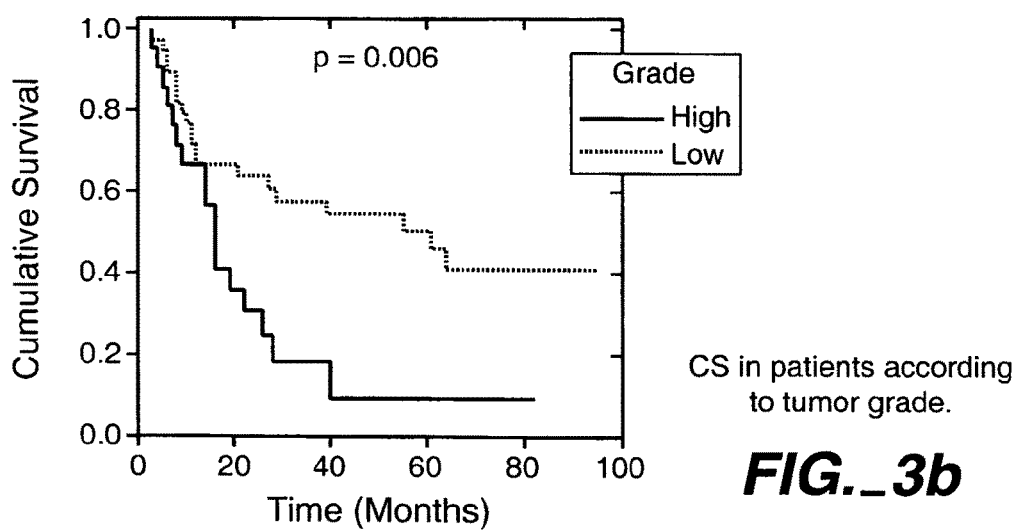
CS in patients according to tumor grade.
FIG._3b
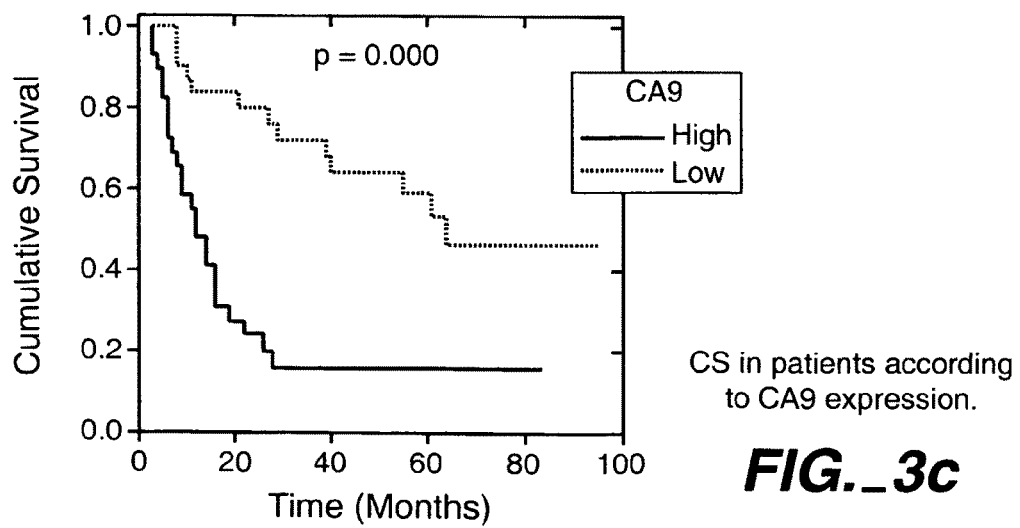
CS in patients according to CA9 expression.
FIG._3c

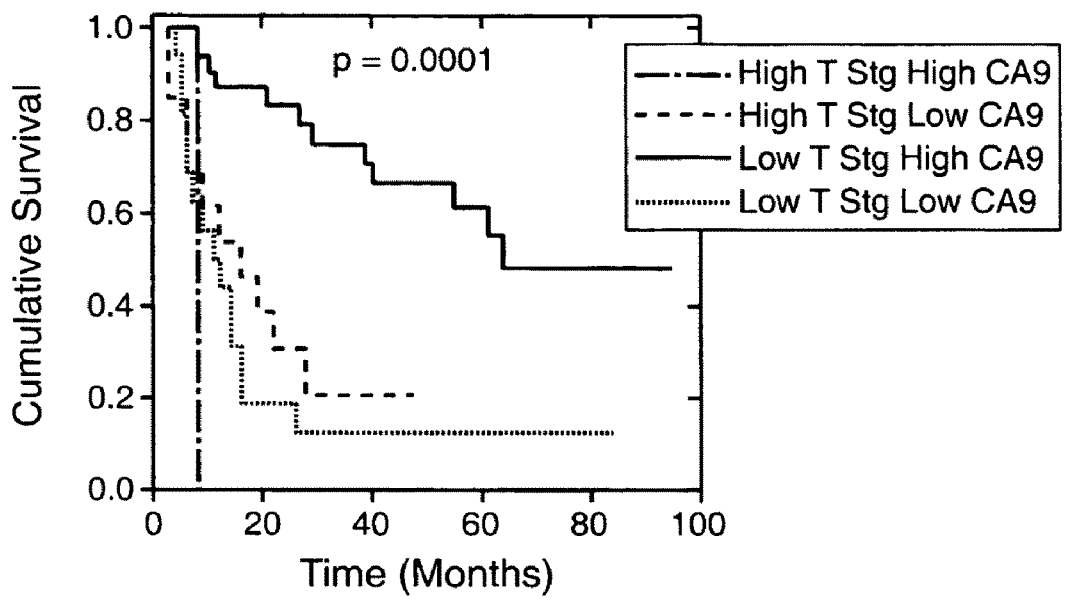
CS in patients according to T stage and CA9 expression.
*FIG._4*
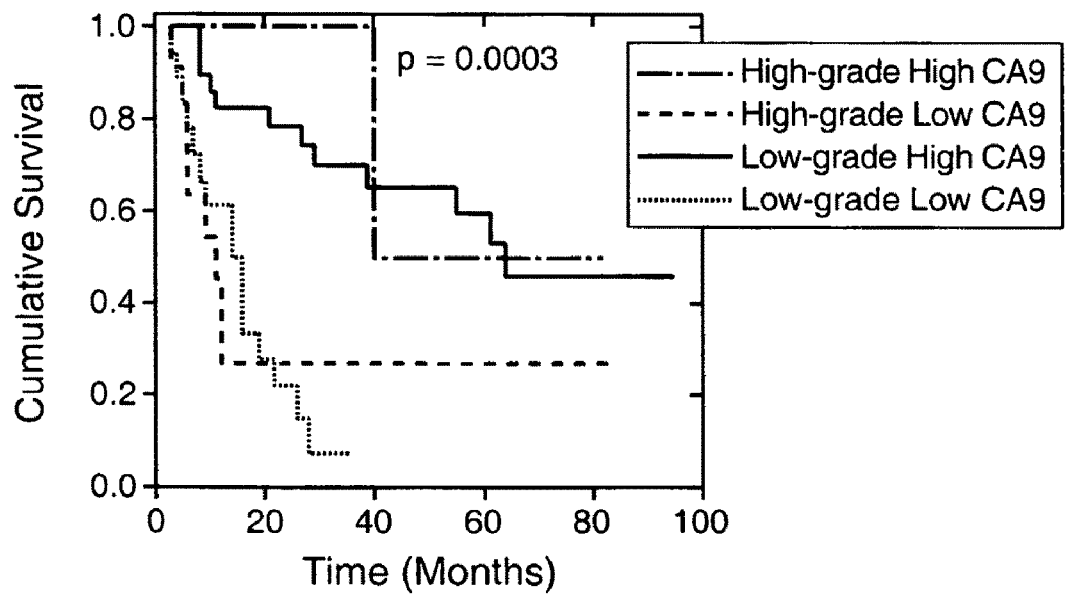
CS in patients according to tumor grade and CA9 expression.
*FIG._5*

SEQUENCE LISTING

<160> NUMBER OF SEQ ID NOS: 11

<210> SEQ ID NO 1
<211> LENGTH: 1522
<212> TYPE: DNA
<213> ORGANISM: Homo sapiens
<220> FEATURE:
<221> NAME/KEY: CDS
<222> LOCATION: (13)..(1389)
<220> FEATURE:
<221> NAME/KEY: mat_peptide
<222> LOCATION: (124)..(1389)

<400> SEQUENCE: 1

```
acagtcagcc gc atg gct ccc ctg tgc ccc agc ccc tgg ctc cct ctg ttg      51
           Met Ala Pro Leu Cys Pro Ser Pro Trp Leu Pro Leu Leu
               -35             -30             -25 atc ccg gcc cct gct cca ggc ctc act gtg caa ctg ctg tca ctg            99
Ile Pro Ala Pro Ala Pro Gly Leu Thr Val Gln Leu Leu Ser Leu
            -20             -15             -10 ctg ctt ctg atg cct gtc cat ccc cag agg ttg ccc cgg atg cag gag       147
Leu Leu Leu Met Pro Val His Pro Gln Arg Leu Pro Arg Met Gln Glu
            -5              -1  1               5 gat tcc ccc ttg gga gga ggc tct tct ggg gaa gat gac cca ctg ggc       195
Asp Ser Pro Leu Gly Gly Gly Ser Ser Gly Glu Asp Asp Pro Leu Gly
        10              15              20 gag gag gat ctg ccc agt gaa gag gat tca ccc aga gag gag gat cca       243
Glu Glu Asp Leu Pro Ser Glu Glu Asp Ser Pro Arg Glu Glu Asp Pro
25              30              35              40 ccc gga gag gag gat cta cct gga gag gag gat cta cct gga gag gag       291
Pro Gly Glu Glu Asp Leu Pro Gly Glu Glu Asp Leu Pro Gly Glu Glu
            45              50              55 gat cta cct gaa gtt aag cct aaa tca gaa gaa gag ggc tcc ctg aag       339
Asp Leu Pro Glu Val Lys Pro Lys Ser Glu Glu Glu Gly Ser Leu Lys
60              65              70 tta gag gat cta cct act gtt gag gct cct gga gat cct caa gaa ccc       387
Leu Glu Asp Leu Pro Thr Val Glu Ala Pro Gly Asp Pro Gln Glu Pro
            75              80              85 cag aat aat gcc cac agg gac aaa gaa ggg gat gac cag agt cat tgg       435
Gln Asn Asn Ala His Arg Asp Lys Glu Gly Asp Asp Gln Ser His Trp
        90              95              100 cgc tat gga ggc gac ccg ccc tgg ccc cgg gtg tcc cca gcc tgc gcg       483
Arg Tyr Gly Gly Asp Pro Pro Trp Pro Arg Val Ser Pro Ala Cys Ala
105             110             115             120 ggc cgc ttc cag tcc ccg gtg gat atc cgc ccc cag ctc gcc gcc ttc       531
Gly Arg Phe Gln Ser Pro Val Asp Ile Arg Pro Gln Leu Ala Ala Phe
            125             130             135 tgc ccg gcc ctg cgc ccc ctg gaa ctc ctg ggc ttc cag ctc ccg ccg       579
Cys Pro Ala Leu Arg Pro Leu Glu Leu Leu Gly Phe Gln Leu Pro Pro
        140             145             150 ctc cca gaa ctg cgc ctg cgc aac aat ggc cac agt gtg caa ctg acc       627
Leu Pro Glu Leu Arg Leu Arg Asn Asn Gly His Ser Val Gln Leu Thr
            155             160             165 ctg cct cct ggg cta gag atg gct ctg ggt ccc ggg cgg gag tac cgg       675
Leu Pro Pro Gly Leu Glu Met Ala Leu Gly Pro Gly Arg Glu Tyr Arg
        170             175             180 gct ctg cag ctg cat ctg cac tgg ggg gct gca ggt cgt ccg ggc tcg       723
Ala Leu Gln Leu His Leu His Trp Gly Ala Ala Gly Arg Pro Gly Ser
185             190             195             200 gag cac act gtg gaa ggc cac cgt ttc cct gcc gag atc cac gtg gtt       771
Glu His Thr Val Glu Gly His Arg Phe Pro Ala Glu Ile His Val Val
            205             210             215 cac ctc agc acc gcc ttt gcc aga gtt gac gag gcc ttg ggg cgc ccg       819
His Leu Ser Thr Ala Phe Ala Arg Val Asp Glu Ala Leu Gly Arg Pro
        220             225             230 gga ggc ctg gcc gtg ttg gcc gcc ttt ctg gag gag ggc ccg gaa gaa       867
Gly Gly Leu Ala Val Leu Ala Ala Phe Leu Glu Glu Gly Pro Glu Glu
            235             240             245 aac agt gcc tat gag cag ttg ctg tct cgc ttg gaa gaa atc gct gag       915
Asn Ser Ala Tyr Glu Gln Leu Leu Ser Arg Leu Glu Glu Ile Ala Glu
250             255             260 gaa ggc tca gag act cag gtc cca gga ctg gac ata tct gca ctc ctg       963
Glu Gly Ser Glu Thr Gln Val Pro Gly Leu Asp Ile Ser Ala Leu Leu
```

```
Glu Gly Ser Glu Thr Gln Val Pro Gly Leu Asp Ile Ser Ala Leu Leu
265                 270                 275                 280 ccc tct gac ttc agc cgc tac ttc caa tat gag ggg tct ctg act aca    1011
Pro Ser Asp Phe Ser Arg Tyr Phe Gln Tyr Glu Gly Ser Leu Thr Thr
                285                 290                 295 ccg ccc tgt gcc cag ggt gtc atc tgg act gtg ttt aac cag aca gtg    1059
Pro Pro Cys Ala Gln Gly Val Ile Trp Thr Val Phe Asn Gln Thr Val
            300                 305                 310 atg ctg agt gct aag cag ctc cac acc ctc tct gac acc ctg tgg gga    1107
Met Leu Ser Ala Lys Gln Leu His Thr Leu Ser Asp Thr Leu Trp Gly
        315                 320                 325 cct ggt gac tct cgg cta cag ctg aac ttc cga gcg acg cag cct ttg    1155
Pro Gly Asp Ser Arg Leu Gln Leu Asn Phe Arg Ala Thr Gln Pro Leu
    330                 335                 340 aat ggg cga gtg att gag gcc tcc ttc cct gct gga gtg gac agc agt    1203
Asn Gly Arg Val Ile Glu Ala Ser Phe Pro Ala Gly Val Asp Ser Ser
345                 350                 355                 360 cct cgg gct gct gag cca gtc cag ctg aat tcc tgc ctg gct gct ggt    1251
Pro Arg Ala Ala Glu Pro Val Gln Leu Asn Ser Cys Leu Ala Ala Gly
                365                 370                 375 gac atc cta gcc ctg gtt ttt ggc ctc ctt ttt gct gtc acc agc gtc    1299
Asp Ile Leu Ala Leu Val Phe Gly Leu Leu Phe Ala Val Thr Ser Val
            380                 385                 390 gcg ttc ctt gtg cag atg aga agg cag cac aga agg gga acc aaa ggg    1347
Ala Phe Leu Val Gln Met Arg Arg Gln His Arg Arg Gly Thr Lys Gly
        395                 400                 405 ggt gtg agc tac cgc cca gca gag gta gcc gag act gga gcc            1389
Gly Val Ser Tyr Arg Pro Ala Glu Val Ala Glu Thr Gly Ala
    410                 415                 420 tagaggctgg atcttggaga atgtgagaag ccagccagag gcatctgagg gggagccggt    1449
aactgtcctg tcctgctcat tatgccactt ccttttaact gccaagaaat ttttttaaaat   1509 aaatatttat aat                                                        1522

<210> SEQ ID NO 2
<211> LENGTH: 459
<212> TYPE: PRT
<213> ORGANISM: Homo sapiens

<400> SEQUENCE: 2

Met Ala Pro Leu Cys Pro Ser Pro Trp Leu Pro Leu Leu Ile Pro Ala
        -35                 -30                 -25

Pro Ala Pro Gly Leu Thr Val Gln Leu Leu Leu Ser Leu Leu Leu Leu
    -20                 -15                 -10

Met Pro Val His Pro Gln Arg Leu Pro Arg Met Gln Glu Asp Ser Pro
-5              -1  1               5                   10

Leu Gly Gly Gly Ser Ser Gly Glu Asp Asp Pro Leu Gly Glu Glu Asp
                15                  20                  25

Leu Pro Ser Glu Glu Asp Ser Pro Arg Glu Glu Asp Pro Gly Glu
            30                  35                  40

Glu Asp Leu Pro Gly Glu Glu Asp Leu Pro Gly Glu Glu Asp Leu Pro
    45                  50                  55

Glu Val Lys Pro Lys Ser Glu Glu Glu Gly Ser Leu Lys Leu Glu Asp
60                  65                  70                  75

Leu Pro Thr Val Glu Ala Pro Gly Asp Pro Gln Glu Pro Gln Asn Asn
                80                  85                  90

Ala His Arg Asp Lys Glu Gly Asp Asp Gln Ser His Trp Arg Tyr Gly
            95                  100                 105
```

Gly Asp Pro Pro Trp Pro Arg Val Ser Pro Ala Cys Ala Gly Arg Phe
            110                 115                 120

Gln Ser Pro Val Asp Ile Arg Pro Gln Leu Ala Ala Phe Cys Pro Ala
        125                 130                 135

Leu Arg Pro Leu Glu Leu Leu Gly Phe Gln Leu Pro Pro Leu Pro Glu
140                 145                 150                 155

Leu Arg Leu Arg Asn Asn Gly His Ser Val Gln Leu Thr Leu Pro Pro
                160                 165                 170

Gly Leu Glu Met Ala Leu Gly Pro Gly Arg Glu Tyr Arg Ala Leu Gln
            175                 180                 185

Leu His Leu His Trp Gly Ala Ala Gly Arg Pro Gly Ser Glu His Thr
        190                 195                 200

Val Glu Gly His Arg Phe Pro Ala Glu Ile His Val His Leu Ser
205                 210                 215

Thr Ala Phe Ala Arg Val Asp Glu Ala Leu Gly Arg Pro Gly Gly Leu
220                 225                 230                 235

Ala Val Leu Ala Ala Phe Leu Glu Glu Gly Pro Glu Glu Asn Ser Ala
                240                 245                 250

Tyr Glu Gln Leu Leu Ser Arg Leu Glu Glu Ile Ala Glu Glu Gly Ser
            255                 260                 265

Glu Thr Gln Val Pro Gly Leu Asp Ile Ser Ala Leu Leu Pro Ser Asp
        270                 275                 280

Phe Ser Arg Tyr Phe Gln Tyr Glu Gly Ser Leu Thr Thr Pro Pro Cys
285                 290                 295

Ala Gln Gly Val Ile Trp Thr Val Phe Asn Gln Thr Val Met Leu Ser
300                 305                 310                 315

Ala Lys Gln Leu His Thr Leu Ser Asp Thr Leu Trp Gly Pro Gly Asp
                320                 325                 330

Ser Arg Leu Gln Leu Asn Phe Arg Ala Thr Gln Pro Leu Asn Gly Arg
            335                 340                 345

Val Ile Glu Ala Ser Phe Pro Ala Gly Val Asp Ser Ser Pro Arg Ala
        350                 355                 360

Ala Glu Pro Val Gln Leu Asn Ser Cys Leu Ala Ala Gly Asp Ile Leu
365                 370                 375

Ala Leu Val Phe Gly Leu Leu Phe Ala Val Thr Ser Val Ala Phe Leu
380                 385                 390                 395

Val Gln Met Arg Arg Gln His Arg Arg Gly Thr Lys Gly Gly Val Ser
                400                 405                 410

Tyr Arg Pro Ala Glu Val Ala Glu Thr Gly Ala
            415                 420

<210> SEQ ID NO 3
<211> LENGTH: 10898
<212> TYPE: DNA
<213> ORGANISM: Homo sapiens
<220> FEATURE:
<221> NAME/KEY: gene
<222> LOCATION: (1)..(10898)
<220> FEATURE:
<221> NAME/KEY: misc_feature
<222> LOCATION: (1974)..(1974)
<223> OTHER INFORMATION: n is a, c, g, or t

<400> SEQUENCE: 3
ggatcctgtt gactcgtgac cttaccccca accctgtgct ctctgaaaca tgagctgtgt      60
ccactcaggg ttaaatggat taagggcggt gcaagatgtg ctttgttaaa cagatgcttg     120

```
aaggcagcat gctcgttaag agtcatcacc aatccctaat ctcaagtaat cagggacaca    180
aacactgcgg aaggccgcag ggtcctctgc ctaggaaaac cagagacctt tgttcacttg    240
tttatctgac cttccctcca ctattgtcca tgaccctgcc aaatccccct ctgtgagaaa    300
cacccaagaa ttatcaataa aaaataaat ttaaaaaaaa aatacaaaaa aaaaaaaaa     360 aaaaaaaaaa gacttacgaa tagttattga taaatgaata gctattggta aagccaagta   420
aatgatcata ttcaaaacca gacggccatc atcacagctc aagtctacct gatttgatct   480
ctttatcatt gtcattcttt ggattcacta gattagtcat catcctcaaa attctccccc   540
aagttctaat tacgttccaa acatttaggg gttacatgaa gcttgaacct actaccttct   600
ttgcttttga gccatgagtt gtaggaatga tgagtttaca ccttacatgc tggggattaa   660
tttaaacttt acctctaagt cagttgggta gcctttggct tattttttgta gctaattttg  720 tagttaatgg atgcactgtg aatcttgcta tgatagtttt cctccacact ttgccactag   780
gggtaggtag gtactcagtt ttcagtaatt gcttacctaa gaccctaagc cctatttctc   840
ttgtactggc ctttatctgt aatatgggca tatttaatac aatataattt ttggagtttt   900
tttgtttgtt tgtttgtttg ttttttttgag acggagtctt gcatctgtca tgcccaggct  960
ggagtagcag tggtgccatc tcggctcact gcaagctcca cctcccgagt tcacgccatt   1020
ttcctgcctc agcctcccga gtagctggga ctacaggcgc ccgccaccat gcccggctaa  1080 tttttttgtat ttttggtaga gacggggttt caccgtgtta gccagaatgg tctcgatctc 1140
ctgacttcgt gatccacccg cctcggcctc ccaaagttct gggattacag gtgtgagcca  1200
ccgcacctgg ccaatttttt gagtctttta agtaaaaat atgtcttgta agctggtaac   1260
tatggtacat ttccttttat taatgtgtg ctgacggtca tataggttct tttgagtttg   1320
gcatgcatat gctactttttt gcagtccttt cattacattt ttctctcttc atttgaagag  1380
catgttatat cttttagctt cacttggctt aaaaggttct ctcattagcc taacacagtg   1440
tcattgttgg taccacttgg atcataagtg gaaaaacagt caagaaattg cacagtaata  1500
cttgtttgta agagggatga ttcaggtgaa tctgacacta agaaactccc ctacctgagg  1560
tctgagattc ctctgacatt gctgtatata ggcttttcct ttgacagcct gtgactgcgg  1620 actattttttc ttaagcaaga tatgctaaag ttttgtgagc ctttttccag agagaggtct  1680
catatctgca tcaagtgaga acatataatg tctgcatgtt tccatatttc aggaatgttt  1740
gcttgtgttt tatgctttta tatagacagg gaaacttgtt cctcagtgac caaaagagg    1800 tgggaattgt tattggatat catcattggc ccacgctttc tgaccttgga aacaattaag  1860
ggttcataat ctcaattctg tcagaattgg tacaagaaat agctgctatg tttcttgaca  1920
ttccacttgg taggaaataa gaatgtgaaa ctcttcagtt ggtgtgtgtc cctngttttt   1980
ttgcaatttc cttcttactg tgttaaaaaa aagtatgatc ttgctctgag aggtgaggca  2040
ttcttaatca tgatctttaa agatcaataa tataatcctt tcaaggatta tgtctttatt  2100
ataataaaga taatttgtct ttaacagaat caataatata atcccttaaa ggattatatc  2160
tttgctgggc gcagtggctc acacctgtaa tcccagcact ttgggtggcc aaggtggaag  2220
gatcaaattt gcctacttct atattatctt ctaaagcaga attcatctct cttccctcaa  2280
tatgatgata ttgacagggt tgccctcac tcactagatt gtgagctcct gctcagggca   2340
ggtagcgttt tttgttttttg tttttgtttt tcttttttga cagggtct tgctctgtca    2400 cccaggccag agtgcaatgg tacagtctca gctcactgca gcctcaaccg cctcggctca  2460
```

```
aaccatcatc ccatttcagc ctcctgagta gctgggacta caggcacatg ccattacacc    2520
tggctaattt ttttgtattt ctagtagaga cagggtttgg ccatgttgcc cgggctggtc    2580
tcgaactcct ggactcaagc aatccaccca cctcagcctc ccaaaatgag gaccgtgtc     2640 ttattcattt ccatgtccct agtccatagc ccagtgctgg acctatggta gtactaaata    2700
aatatttgtt gaatgcaata gtaaatagca tttcagggag caagaactag attaacaaag    2760
gtggtaaaag gtttggagaa aaaaataata gtttaatttg gctagagtat gagggagagt    2820
agtaggagac aagatggaaa ggtctcttgg gcaaggtttt gaaggaagtt ggaagtcaga    2880
agtacacaat gtgcatatcg tggcaggcag tggggagcca atgaaggctt ttgagcagga    2940
gagtaatgtg ttgaaaaata aatataggtt aaacctatca gagcccctct gacacataca    3000
cttgcttttc attcaagctc aagtttgtct cccacatacc cattacttaa ctcaccctcg    3060
ggctccccta gcagcctgcc ctacctcttt acctgcttcc tggtggagtc agggatgtat    3120
acatgagctg ctttcccctct cagccagagg acatgggggg ccccagctcc cctgcctttc    3180
cccttctgtg cctggagctg ggaagcaggc cagggttagc tgaggctggc tggcaagcag    3240
ctgggtggtg ccaggagag cctgcatagt gccaggtggt gccttgggtt ccaagctagt     3300
ccatggcccc gataaccttc tgcctgtgca cacacctgcc cctcactcca cccccatcct    3360
agctttggta tggggagag ggcacagggc cagacaaacc tgtgagactt tggctccatc     3420
tctgcaaaag ggcgctctgt gagtcagcct gctcccctcc aggcttgctc ctcccccacc    3480
cagctctcgt ttccaatgca cgtacagccc gtacacaccg tgtgctggga cacccccacag   3540 tcagccgcat ggctcccctg tgccccagcc cctggctccc tctgttgatc ccggcccctg    3600
ctccaggcct cactgtgcaa ctgctgctgt cactgctgct tctggtgcct gtccatcccc    3660
agaggttgcc ccggatgcag gaggattccc ccttgggagg aggctcttct ggggaagatg    3720
acccactggg cgaggaggat ctgcccagtg aagaggattc acccagagag gaggatccac    3780
ccggagagga ggatctacct ggagaggagg atctacctgg agaggaggat ctacctgaag    3840
ttaagcctaa atcagaagaa gagggctccc tgaagttaga ggatctacct actgttgagg    3900
ctcctggaga tcctcaagaa ccccagaata atgcccacag ggacaaagaa ggtaagtggt    3960
catcaatctc caaatccagg ttccaggagg ttcatgactc ccctcccata ccccagccta    4020
ggctctgttc actcagggaa ggaggggaga ctgtactccc cacagaagcc cttccagagg    4080
tcccatacca atatccccat ccccactctc ggaggtagaa agggacagat gtggagagaa    4140
aataaaaagg gtgcaaaagg agagaggtga gctggatgag atgggagaga aggggaggc    4200 tggagaagag aaaggdatga gaactgcaga tgagagaaaa aatgtgcaga cagaggaaaa    4260
aaataggtgg agaaggagag tcagagagtt tgaggggaag agaaaaggaa agcttgggag    4320
gtgaagtggg taccagagac aagcaagaag agctggtaga agtcatctca tcttaggcta    4380
caatgaggaa ttgagaccta ggaagaaggg acacagcagg tagagaaacg tggcttcttg    4440
actcccaagc caggaatttg gggaaagggg ttggagacca tacaaggcag agggatgagt    4500
ggggagaaga aagaagggag aaaggaaaga tggtgtactc actcatttgg gactcaggac    4560
tgaagtgccc actcactttt tttttttttt tttttgagac aaactttcac ttttgttgcc    4620
caggctggag tgcaatggcg cgatctcggc tcactgcaac ctccacctcc cgggttcaag    4680
tgattctcct gcctcagcct ctagccaagt agctgcgatt acaggcatgc gccaccacgc    4740
ccggctaatt tttgtatttt tagtagagac ggggtttcgc catgttggtc aggctggtct    4800
cgaactcctg atctcaggtg atccaaccac cctggcctcc caaagtgctg ggattatagg    4860
```

```
cgtgagccac agcgcctggc ctgaagcagc cactcacttt tacagaccct aagacaatga    4920
ttgcaagctg gtaggattgc tgtttggccc acccagctgc ggtgttgagt ttgggtgcgg    4980
tctcctgtgc tttgcacctg gcccgcttaa ggcatttgtt acccgtaatg ctcctgtaag    5040
gcatctgcgt ttgtgacatc gttttggtcg ccaggaaggg attggggctc taagcttgag    5100
cggttcatcc ttttcattta tacagggat gaccagagtc attggcgcta tggaggtgag     5160
acacccaccc gctgcacaga cccaatctgg gaacccagct ctgtggatct cccctacagc    5220
cgtccctgaa cactggtccc gggcgtccca cccgccgccc accgtcccac ccctcacct    5280 tttctacccg ggttccctaa gttcctgacc taggcgtcag acttcctcac tatactctcc    5340
caccccaggc gacccgccct ggccccgggt gtcccagcc tgcgcgggcc gcttccagtc     5400
cccggtggat atccgccccc agctcgccgc cttctgcccg gccctgcgcc ccctggaact    5460
cctgggcttc cagctcccgc cgctcccaga actgcgcctg cgcaacaatg ccacagtgg    5520 tgaggggggtc tccccgccga gacttgggga tggggcgggg cgcagggaag ggaaccgtcg    5580
cgcagtgcct gcccgggggt gggctggcc ctaccgggcg gggccggctc acttgcctct     5640
ccctacgcag tgcaactgac cctgcctcct gggctagaga tggctctggg tcccgggcgg    5700
gagtaccggg ctctgcagct gcatctgcac tgggggggctg caggtcgtcc gggctcggag    5760
cacactgtgg aaggccaccg tttccctgcc gaggtgagcg cggactggcc gagaaggggc    5820
aaaggagcgg ggcggacggg ggccagagac gtggccctct cctaccctcg tgtccttttc    5880
agatccacgt ggttcacctc agcaccgcct ttgccagagt tgacgaggcc ttggggcgcc    5940
cgggaggcct ggccgtgttg gccgccttc tggaggtacc agatcctgga cacccccta     6000 tccccgcttt cccatcccat gctcctcccg gactctatcg tggagccaga gaccccatcc    6060
cagcaagctc actcaggccc ctggctgaca aactcattca cgcactgttt gttcatttaa    6120
cacccactgt gaaccaggca ccagccccca acaaggattc tgaagctgta ggtccttgcc    6180
tctaaggagc ccacagccag tgggggaggc tgacatgaca gacacatagg aaggacatag    6240
taaagatggt ggtcacagag gaggtgacac ttaaagcctt cactggtaga aaagaaaagg    6300
aggtgttcat tgcagaggaa acagaatgtg caaagactca gaatatggcc tatttaggga    6360
atggctacat acaccatgat tagaggaggc ccagtaaagg gaagggatgg tgagatgcct    6420
gctaggttca ctcactcact tttatttatt tatttatttt tttgacagtc tctctgtcgc    6480
ccaggctgga gtgcagtggt gtgatcttgg gtcactgcaa cttccgcctc ccgggttcaa    6540
gggattctcc tgcctcagct tcctgagtag ctgggggttac aggtgtgtgc caccatgccc    6600
agctaatttt ttttttgtatt tttagtagac agggtttcac catgttggtc aggctggtct    6660
caaactcctg gcctcaagtg atccgcctga ctcagcctac caaagtgctg attacaagtg    6720
tgagccaccg tgcccagcca cactcactga ttctttaatg ccagccacac agcacaaagt    6780
tcagagaaat gcctccatca tagcatgtca atatgttcat actcttaggt tcatgatgtt    6840
cttaacatta ggttcataag caaaataaga aaaagaata ataaataaaa gaagtggcat    6900
gtcaggacct cacctgaaaa gccaaacaca gaatcatgaa ggtgaatgca gaggtgacac    6960
caacacaaag gtgtatatat ggtttcctgt ggggagtatg tacggaggca gcagtgagtg    7020
agactgcaaa cgtcagaagg gcacgggtca ctgagagcct agtatcctag taaagtgggc    7080
tctctccctc tctctccagc ttgtcattga aaaccagtcc accaagcttg ttggttcgca    7140
cagcaagagt acatagagtt tgaaataata cataggattt taagagggag acactgtctc    7200
```

-continued

```
taaaaaaaaa aacaacagca acaacaaaaa gcaacaacca ttacaatttt atgttccctc    7260
agcattctca gagctgagga atgggagagg actatgggaa ccccctccat gttccggcct    7320
tcagccatgg ccctggatac atgcactcat ctgtcttaca atgtcattcc cccaggaggg    7380
cccggaagaa aacagtgcct atgagcagtt gctgtctcgc ttggaagaaa tcgctgagga    7440
aggtcagttt gttggtctgg ccactaatct ctgtggccta gttcataaag aatcacccct    7500
tggagcttca ggtctgaggc tggagatggg ctccctccag tgcaggaggg attgaagcat    7560
gagccagcgc tcatcttgat aataaccatg aagctgacag acacagttac ccgcaaacgg    7620
ctgcctacag attgaaaacc aagcaaaaac cgccgggcac ggtggctcac gcctgtaatc    7680
ccagcacttt gggaggccaa ggcaggtgga tcacgaggtc aagagatcaa gaccatcctg    7740
gccaacatgg tgaaacccca tctctactaa aaatacgaaa aaatagccag gcgtggtggc    7800
gggtgcctgt aatcccagct actcgggagg ctgaggcagg agaatggcat gaacccggga    7860
ggcagaagtt gcagtgagcc gagatcgtgc cactgcactc cagcctgggc aacagagcga    7920
gactcttgtc tcaaaaaaaa aaaaaaaaa gaaaaccaag caaaaaccaa aatgagacaa    7980
aaaaacaag accaaaaaat ggtgtttgga aattgtcaag gtcaagtctg gagagctaaa    8040
cttttttctga gaactgttta tctttaataa gcatcaaata ttttaacttt gtaaatactt    8100
ttgttggaaa tcgttctctt cttagtcact cttgggtcat tttaaatctc acttactcta    8160
ctagaccttt taggtttctg ctagactagg tagaactctg cctttgcatt tcttgtgtct    8220
gttttgtata gttatcaata ttcatattta tttacaagtt attcagatca ttttttcttt    8280
tctttttttt tttttttttt tttttacat ctttagtaga gacagggttt caccatattg    8340
gccaggctgc tctcaaactc ctgaccttgt gatccaccag cctcggcctc ccaaagtgct    8400
gggattcatt ttttctttt aatttgctct gggcttaaac ttgtggccca gcactttatg    8460
atggtacaca gagttaagag tgtagactca gacggtcttt cttctttcct tctcttcctt    8520
cctcccttcc ctcccacctt cccttctctc cttcctttct ttcttcctct cttgcttcct    8580
caggcctctt ccagttgctc caaagccctg tactttttt tgagttaacg tcttatggga    8640
agggcctgca cttagtgaag aagtggtctc agagttgagt taccttggct tctgggaggt    8700
gaaactgtat ccctatacc tgaagcttta aggggtgca atgtagatga accccaaca    8760
tagatcctct tcacaggctc agagactcag gtcccaggac tggacatatc tgcactcctg    8820
ccctctgact tcagccgcta cttccaatat gaggggtctc tgactacacc gccctgtgcc    8880
cagggtgtca tctggactgt gtttaaccag acagtgatgc tgagtgctaa gcaggtgggc    8940
ctggggtgtg tgtggacaca gtgggtgcgg gggaaagagg atgtaagatg agatgagaaa    9000
caggagaaga aagaaatcaa ggctgggctc tgtggcttac gcctataatc ccaccacgtt    9060
gggaggctga ggtgggagaa tggtttgagc ccaggagttc aagacaaggc ggggcaacat    9120
agtgtgaccc catctctacc aaaaaaaccc caacaaaacc aaaatagccc gggcatggtg    9180
gtatgcggcc tagtcccagc tactcaagga ggctgaggtg ggaagatcgc ttgattccag    9240
gagtttgaga ctgcagtgag ctatgatccc accactgcct accatctta ggatacattt    9300
atttatttat aaaagaaatc aagaggctgg atggggaata caggagctgg agggtggagc    9360
cctgaggtgc tggttgtgag ctggcctggg acccttgttt cctgtcatgc catgaaccca    9420
cccacactgt ccactgacct ccctagctcc acaccctctc tgacaccctg tggggacctg    9480
gtgactctcg gctacagctg aacttccgag cgacgcagcc tttgaatggg cgagtgattg    9540
aggcctcctt ccctgctgga gtggacagca gtcctcgggc tgctgagcca ggtacagctt    9600
```

-continued

```
tgtctggttt cccccagcc agtagtccct tatcctccca tgtgtgtgcc agtgtctgtc    9660
attggtggtc acagcccgcc tctcacatct ccttttctc tccagtccag ctgaattcct    9720
gcctggctgc tggtgagtct gccctcctc ttggtcctga tgccaggaga ctcctcagca    9780
ccattcagcc ccagggctgc tcaggaccgc ctctgctccc tctccttttc tgcagaacag    9840
accccaaccc caatattaga gaggcagatc atggtgggga ttcccccatt gtccccagag    9900
gctaattgat tagaatgaag cttgagaaat ctcccagcat ccctctcgca aaagaatccc    9960
cccccttttt tttaaagata gggtctcact ctgtttgccc caggctgggg tgttgtggca    10020
cgatcatagc tcactgcagc ctcgaactcc taggctcagg caatcctttc accttagctt    10080
ctcaaagcac tgggactgta ggcatgagcc actgtgcctg ccccaaacg ccccttttac    10140 ttggctttta ggaagcaaaa acggtgctta tcttaccct tctcgtgtat ccaccctcat    10200 cccttgctg gcctcttctg gagactgagg cactatgggg ctgcctgaga actcggggca    10260
ggggtggtgg agtgcactga ggcaggtgtt gaggaactct gcagacccct cttccttccc    10320
aaagcagccc tctctgctct ccatcgcagg tgacatccta gccctggttt ttggcctcct    10380
ttttgctgtc accagcgtcg cgttccttgt gcagatgaga aggcagcaca ggtattacac    10440
tgaccctttc ttcaggcaca agcttccccc acccttgtgg agtcacttca tgcaaagcgc    10500
atgcaaatga gctgctcctg ggccagtttt ctgattagcc tttcctgttg tgtacacaca    10560 gaagggaac caaaggggt gtgagctacc gcccagcaga ggtagccgag actggagcct    10620
agaggctgga tcttggagaa tgtgagaagc cagccgagg catctgaggg ggagccggta    10680
actgtcctgt cctgctcatt atgccacttc cttttaactg ccaagaaatt ttttaaaata    10740
aatatttata ataaaatatg tgttagtcac ctttgttccc caaatcagaa ggaggtattt    10800
gaatttccta ttactgttat tagcaccaat ttagtggtaa tgcatttatt ctattacagt    10860
tcggcctcct tccacacatc actccaatgt gttgctcc                           10898
```

<210> SEQ ID NO 4
<211> LENGTH: 59
<212> TYPE: PRT
<213> ORGANISM: Homo sapiens

<400> SEQUENCE: 4

```
Ser Ser Gly Glu Asp Asp Pro Leu Gly Glu Glu Asp Leu Pro Ser Glu
1               5                   10                  15

Glu Asp Ser Pro Arg Glu Glu Asp Pro Gly Glu Glu Asp Leu Pro
            20                  25                  30

Gly Glu Glu Asp Leu Pro Gly Glu Glu Asp Leu Pro Glu Val Lys Pro
        35                  40                  45

Lys Ser Glu Glu Glu Gly Ser Leu Lys Leu Glu
    50                  55
```

<210> SEQ ID NO 5
<211> LENGTH: 257
<212> TYPE: PRT
<213> ORGANISM: Homo sapiens

<400> SEQUENCE: 5

```
Gly Asp Asp Gln Ser His Trp Arg Tyr Gly Gly Asp Pro Pro Trp Pro
1               5                   10                  15

Arg Val Ser Pro Ala Cys Ala Gly Arg Phe Gln Ser Pro Val Asp Ile
            20                  25                  30
```

-continued

```
Arg Pro Gln Leu Ala Ala Phe Cys Pro Ala Leu Arg Pro Leu Glu Leu
         35                  40                  45

Leu Gly Phe Gln Leu Pro Pro Leu Pro Glu Leu Arg Leu Arg Asn Asn
 50                  55                  60

Gly His Ser Val Gln Leu Thr Leu Pro Pro Gly Leu Glu Met Ala Leu
 65                  70                  75                  80

Gly Pro Gly Arg Glu Tyr Arg Ala Leu Gln Leu His Leu His Trp Gly
                 85                  90                  95

Ala Ala Gly Arg Pro Gly Ser Glu His Thr Val Glu Gly His Arg Phe
                 100                 105                 110

Pro Ala Glu Ile His Val Val His Leu Ser Thr Ala Phe Ala Arg Val
                 115                 120                 125

Asp Glu Ala Leu Gly Arg Pro Gly Gly Leu Ala Val Leu Ala Ala Phe
130                 135                 140

Leu Glu Glu Gly Pro Glu Glu Asn Ser Ala Tyr Glu Gln Leu Leu Ser
145                 150                 155                 160

Arg Leu Glu Glu Ile Ala Glu Gly Ser Glu Thr Gln Val Pro Gly
                 165                 170                 175

Leu Asp Ile Ser Ala Leu Leu Pro Ser Asp Phe Ser Arg Tyr Phe Gln
                 180                 185                 190

Tyr Glu Gly Ser Leu Thr Thr Pro Pro Cys Ala Gln Gly Val Ile Trp
                 195                 200                 205

Thr Val Phe Asn Gln Thr Val Met Leu Ser Ala Lys Gln Leu His Thr
                 210                 215                 220

Leu Ser Asp Thr Leu Trp Gly Pro Gly Asp Ser Arg Leu Gln Leu Asn
225                 230                 235                 240

Phe Arg Ala Thr Gln Pro Leu Asn Gly Arg Val Ile Glu Ala Ser Phe
                 245                 250                 255

Pro

<210> SEQ ID NO 6
<211> LENGTH: 37
<212> TYPE: PRT
<213> ORGANISM: Homo sapiens

<400> SEQUENCE: 6

Met Ala Pro Leu Cys Pro Ser Pro Trp Leu Pro Leu Leu Ile Pro Ala
 1               5                  10                  15

Pro Ala Pro Gly Leu Thr Val Gln Leu Leu Leu Ser Leu Leu Leu Leu
                 20                  25                  30

Met Pro Val His Pro
         35

<210> SEQ ID NO 7
<211> LENGTH: 377
<212> TYPE: PRT
<213> ORGANISM: Homo sapiens

<400> SEQUENCE: 7

Gln Arg Leu Pro Arg Met Gln Glu Asp Ser Pro Leu Gly Gly Gly Ser
 1               5                  10                  15

Ser Gly Glu Asp Asp Pro Leu Gly Glu Glu Asp Leu Pro Ser Glu Glu
                 20                  25                  30

Asp Ser Pro Arg Glu Glu Asp Pro Pro Gly Glu Glu Asp Leu Pro Gly
                 35                  40                  45

Glu Glu Asp Leu Pro Gly Glu Glu Asp Leu Pro Glu Val Lys Pro Lys
```

-continued

```
                  50                  55                  60
Ser Glu Glu Gly Ser Leu Lys Leu Glu Asp Leu Pro Thr Val Glu
 65                  70                  75                  80

Ala Pro Gly Asp Pro Gln Glu Pro Gln Asn Asn Ala His Arg Asp Lys
                 85                  90                  95

Glu Gly Asp Asp Gln Ser His Trp Arg Tyr Gly Gly Asp Pro Pro Trp
                100                 105                 110

Pro Arg Val Ser Pro Ala Cys Ala Gly Arg Phe Gln Ser Pro Val Asp
                115                 120                 125

Ile Arg Pro Gln Leu Ala Ala Phe Cys Pro Ala Leu Arg Pro Leu Glu
            130                 135                 140

Leu Leu Gly Phe Gln Leu Pro Pro Leu Pro Glu Leu Arg Leu Arg Asn
145                 150                 155                 160

Asn Gly His Ser Val Gln Leu Thr Leu Pro Pro Gly Leu Glu Met Ala
                165                 170                 175

Leu Gly Pro Gly Arg Glu Tyr Arg Ala Leu Gln Leu His Leu His Trp
            180                 185                 190

Gly Ala Ala Gly Arg Pro Gly Ser Glu His Thr Val Glu Gly His Arg
            195                 200                 205

Phe Pro Ala Glu Ile His Val Val His Leu Ser Thr Ala Phe Ala Arg
            210                 215                 220

Val Asp Glu Ala Leu Gly Arg Pro Gly Gly Leu Ala Val Leu Ala Ala
225                 230                 235                 240

Phe Leu Glu Glu Gly Pro Glu Glu Asn Ser Ala Tyr Glu Gln Leu Leu
                245                 250                 255

Ser Arg Leu Glu Glu Ile Ala Glu Glu Gly Ser Glu Thr Gln Val Pro
                260                 265                 270

Gly Leu Asp Ile Ser Ala Leu Leu Pro Ser Asp Phe Ser Arg Tyr Phe
            275                 280                 285

Gln Tyr Glu Gly Ser Leu Thr Thr Pro Pro Cys Ala Gln Gly Val Ile
            290                 295                 300

Trp Thr Val Phe Asn Gln Thr Val Met Leu Ser Ala Lys Gln Leu His
305                 310                 315                 320

Thr Leu Ser Asp Thr Leu Trp Gly Pro Gly Asp Ser Arg Leu Gln Leu
                325                 330                 335

Asn Phe Arg Ala Thr Gln Pro Leu Asn Gly Arg Val Ile Glu Ala Ser
                340                 345                 350

Phe Pro Ala Gly Val Asp Ser Ser Pro Arg Ala Ala Glu Pro Val Gln
            355                 360                 365

Leu Asn Ser Cys Leu Ala Ala Gly Asp
    370                 375

<210> SEQ ID NO 8
<211> LENGTH: 20
<212> TYPE: PRT
<213> ORGANISM: Homo sapiens

<400> SEQUENCE: 8

Ile Leu Ala Leu Val Phe Gly Leu Leu Phe Ala Val Thr Ser Val Ala
 1               5                  10                  15

Phe Leu Val Gln
            20

<210> SEQ ID NO 9
<211> LENGTH: 25
```

```
<212> TYPE: PRT
<213> ORGANISM: Homo sapiens

<400> SEQUENCE: 9

Met Arg Arg Gln His Arg Arg Gly Thr Lys Gly Gly Val Ser Tyr Arg
1               5                   10                  15

Pro Ala Glu Val Ala Glu Thr Gly Ala
            20                  25

<210> SEQ ID NO 10
<211> LENGTH: 19
<212> TYPE: DNA
<213> ORGANISM: Homo sapiens

<400> SEQUENCE: 10
aggaggatct gcccagtga                                                   19

<210> SEQ ID NO 11
<211> LENGTH: 19
<212> TYPE: DNA
<213> ORGANISM: Homo sapiens

<400> SEQUENCE: 11
gccaatgact ctggtcatc                                                   19
```

MN/CA IX/CA9 AND RENAL CANCER PROGNOSIS

This application is a continuation of U.S. Ser. No. 11/578,744 (filed Mar. 8, 2007), now U.S. Pat. No. 7,482,129 herein incorporated by reference, which is a national stage filing of PCT/US2005/15587 (filed May 4, 2005), which claims priority from U.S. Provisional Application No. 60/568,019 filed May 4, 2004, now abandoned.

FIELD OF THE INVENTION

The present invention is in the general area of medical genetics and in the fields of biochemical engineering, immunochemistry and oncology. More specifically, it relates to the MN gene—a cellular gene considered to be an oncogene, known alternatively as MN/CA9, CA9, or carbonic anhydrase 9, which gene encodes the oncoprotein now known alternatively as the MN protein, the MN/CA IX isoenzyme, MN/CA IX, carbonic anhydrase IX, CA IX, the MN/G250 or the G250 protein.

More specifically, the instant invention is directed to the identification of MN antigen or MN gene expression in renal cancer patient samples, which provides the basis for prognostic assays for renal cancer, particularly renal clear cell carcinoma, and for making clinical decisions on cancer treatment.

REFERENCE TO SEQUENCE LISTING

Duplicate copies of the Sequence Listing, contained on the two enclosed compact discs and identified as MST-2413-1A.SEQ LISTING, were created on Jan. 14, 2009, are is 31.8 kb in size and is hereby incorporated by reference.

BACKGROUND

As indicated above, the MN gene and protein are known by a number of alternative names, which names are used herein interchangeably. The MN protein was found to bind zinc and have carbonic anhydrase (CA) activity and is now considered to be the ninth carbonic anhydrase isoenzyme—MN/CA IX or CA IX [22]. According to the carbonic anhydrase nomenclature, human CA isoenzymes are written in capital roman letters and numbers, whereas their genes are written in italic letters and arabic numbers. Alternatively, "MN" is used herein to refer either to carbonic anhydrase isoenzyme IX (CA IX) proteins/polypeptides, or carbonic anhydrase isoenzyme 9 (CA9) gene, nucleic acids, cDNA, mRNA etc. as indicated by the context.

The MN protein has also been identified with the G250 antigen. Uemura et al. [23] states: "Sequence analysis and database searching revealed that G250 antigen is identical to MN, a human tumor-associated antigen identified in cervical carcinoma (Pastorek et al., 1994)."

Zavada et al., International Publication No. WO 93/18152 (published Sep. 16, 1993) and U.S. Pat. No. 5,387,676 (issued Feb. 7, 1995) describe the discovery of the MN gene and protein. The MN gene was found to be present in the chromosomal DNA of all vertebrates tested, and its expression to be strongly correlated with tumorigenicity. In general, oncogenesis may be signified by the abnormal expression of CA IX protein. For example, oncogenesis may be signified: (1) when CA IX protein is present in a tissue which normally does not express CA IX protein to any significant degree; (2) when CA IX protein is absent from a tissue that normally expresses it; (3) when CA9 gene expression is at a significantly increased level, or at a significantly reduced level from that normally expressed in a tissue; or (4) when CA IX protein is expressed in an abnormal location within a cell. WO 93/18152 further discloses, among other MN-related inventions, MN/CA IX-specific monoclonal antibodies (MAbs), including the M75 MAb and the VU-M75 hybridoma that secretes the M75 MAb. The M75 MAb specifically binds to immunodominant epitopes on the proteoglycan (PG) domain of the MN/CA IX proteins.

Zavada et al., International Publication No. WO 95/34650 (published Dec. 21, 1995) provides in FIG. 1 the nucleotide sequences for a full-length MN cDNA [SEQ ID NO: 1] clone isolated as described therein, and the amino acid sequence [SEQ ID NO: 2] encoded by that MN cDNA. WO 95/34650 also provides in FIG. 6 the nucleotide sequence for the MN promoter. Those MN cDNA, promoter and amino acid sequences are incorporated by reference herein.

Zavada et al., International Publication No. WO 03/100029 (published Dec. 4, 2003) discloses among other MN-related inventions, MN/CA IX-specific MAbs that are directed to non-immunodominant epitopes, including those on the carbonic anhydrase (CA) domain of the MN/CA IX protein. An example of such a MN/CA IX-specific MAb is the V/10 MAb, secreted from the V/10-VU hybridoma The MN protein is now considered to be the first tumor-associated carbonic anhydrase isoenzyme that has been described. The carbonic anhydrase family (CA) includes eleven catalytically active zinc metalloenzymes involved in the reversible hydration-dehydration of carbon dioxide: $CO_2 + H_2O \Leftrightarrow HCO_3^- + H^+$. CAs are widely distributed in different living organisms. The CAs participate in a variety of physiological and biological processes and show remarkable diversity in tissue distribution, subcellular localization, and biological functions [24, 25, 26]. Carbonic anhydrase IX, CA IX, is one of the most recently identified isoenzymes [22, 27]. Because of the CA IX overexpression in transformed cell lines and in several human malignancies, it has been recognized as a tumor-associated antigen and linked to the development of human cancers [8, 16, 28].

CA IX is a glycosylated transmembrane CA isoform with a unique N-terminal proteoglycan-like extension [22]. Through transfection studies it has been demonstrated that CA IX can induce the transformation of 3T3 cells [22]. Recent studies have revealed that CA IX not only participates in cell adhesion, but also can be induced in hypoxia via the HIF-1 protein binding to the hypoxia-responsive element of the MN promoter [29, 30]. The transcription of the MN gene is negatively regulated by wild-type von Hippel-Lindau tumor suppressor gene in renal cell carcinoma cells [31]. The protein product of the von Hippel-Lindau tumor suppressor gene interacts with the ubiquitin ligase complex that is responsible for targeting HIF-1α for oxygen-dependent proteolysis [32, 33]. Thus, low levels of oxygen lead to stabilization of HIF-1α, which in turn leads to the increased expression of MN [30]. Areas of high expression of MN in cancers are linked to tumor hypoxia as reported in many cancers, and incubation of tumor cells under hypoxic conditions leads to the induction of MN expression [30, 34-38].

Many studies, using the MN-specific monoclonal antibody (MAb) M75, have confirmed the diagnostic/prognostic utility of MN in diagnosing/prognosing precancerous and cancerous cervical lesions [16, 39, 40]. Immunohistochemical studies with the M75 MAb of cervical carcinomas and a PCR-based (RT-PCR) survey of renal cell carcinomas have identified MN expression as closely associated with those cancers and confirm MN's utility as a tumor biomarker [16, 39, 41]. In various cancers (notably uterine cervical, ovarian, endometrial, renal, bladder, breast, colorectal, lung, esophageal, head and neck and prostate cancers, among others), CA IX expression is increased and has been correlated with the microvessel density and the levels of hypoxia in some tumors [34, 35].

In tissues that normally do not express MN protein, CA IX positivity is considered to be diagnostic for preneoplastic/neoplastic diseases, such as, lung, breast and cervical precancers/cancers [36-38], among other precancers/cancers. Very few normal tissues have been found to express MN protein to any significant degree; those MN-expressing normal tissues include the human gastric mucosa and gallbladder epithelium, and some other normal tissues of the alimentary tract [42-44].

Renal cell carcinoma (RCC), which accounts for 3% of all adult malignancies, is the most lethal of the urologic cancers [1]. RCC is, in the US, the ninth leading cause of cancer mortality, with 35,000 new cases and more than 12,000 deaths predicted in 2004 [2]. The incidence of RCC has increased since the 1970s, largely owing to a more prevalent use of ultrasonography and computerized tomography for the evaluation of a variety of abdominal and gastrointestinal complaints [3]. For RCC, the best available prognostic indicator is stage, but the current prognostic factors: Fuhrman grade, and performance status, as well as stage, are insufficient to predict patient outcome and cancer aggressiveness [4-6]. Identification of biomarkers that provide further prognostic information would thus be vital for defining optimal treatment and outcomes.

As indicated above, previous studies have shown that MN, a member of the carbonic anhydrase family, is induced constitutively in certain tumor types but is absent in most normal tissues [7-10]. Furthermore, previous immunobiochemical studies of malignant and benign renal tissues revealed that MN is also highly expressed in RCC, suggesting that MN expression is a useful diagnostic biomarker [11, 12, 15-17]. Bui et al. [17] state that another biomarker Ki67 when used with CA IX in RCC highly predicts survival. In addition, Zavada et al. [18] discovered a soluble form of CA IX in the body fluids (urine and CA IX serum) of RCC patients. [See also, Zavada et al., International Publication No. WO 03/100029 (published Dec. 4, 2003).]

Disclosed herein are methods wherein MN expression is shown to be useful as a prognostic marker for RCC, and particularly renal clear cell carcinoma (CCC). CCCs comprise up to about 85% of RCCs. The experiments disclosed herein support the promising significance of MN as a molecular marker in RCCs, and particularly CCCs. Low MN expression in RCCs, particularly CCCs, was found to be a poor prognostic factor, and conversely high MN expression was found to be a good prognostic factor. MN expression is disclosed herein to be the best prognostic factor when compared with T stage and Fuhrman grade. Decreased MN expression is disclosed herein to be independently associated with poor survival.

The prognostic methods of this invention use 50% MN/CA IX/CA9 expression as the cut-off between better and poorer prognoses for RCCs/CCCs. Liao et al. [12] (at page 2828) described MN/CA IX immunostaining patterns "as diffuse when >50% of the cells stained and focal when ≦50% of the cells stained." Whereas the instant inventive methods use 50% as the cut-off value, Bui et al. [15] (at page 4) found by survival tree analysis of MN/CA IX immunostaining scoring information from tissue arrays "that a staining percentage of 85% was an ideal cutoff for stratification for patient survival." [See also, Bui et al. International Publication No. WO 03/089659 (published Oct. 30, 2003).]

The prognostic methods of this invention can be used to predict clinical outcome and tumor behavior. The prognostic methods disclosed herein detect and/or quantitate levels, extent and/or intensity of MN expression, and can identify high-risk RCC/CCC patients who could benefit from adjuvant immunotherapy and MN/CA IX/CA9-targeted therapies, among other appropriate therapies.

Preliminary data from the Bui et al. [15] study indicate a relationship between MN/CA IX and immunotherapy response. Similarly, therapies based on monoclonal antibodies to MN/CA IX or immunotherapy with MN/CA IX-based RCC vaccine [15, 19-21], as well as vectors that encode a cytotoxic protein/polypeptide and/or cytokine operatively linked to the MN gene promoter or a MN promoter fragment having promoter activity [as disclosed, for example, in Zavada et al., International Publication No. WO 00/24913 (published May 4, 2000)], preferably a MN promoter fragment comprising a hypoxia responsive element (HRE), preferably the MN HRE, can also be considered according to the level and/or extent of MN/CA IX/CA9 expression in a RCC/CCC patient sample.

SUMMARY OF THE INVENTION

The present invention relates to methods for detecting and/or quantitating levels and/or extent of MN/CA9 gene expression products in a sample taken from a patient afflicted with renal cell carcinoma (RCC), particularly from a patient afflicted with renal clear cell carcinoma (CCC), wherein said detecting and/or quantitating is useful in determining the prognosis of the patient. The RCC/CCC patient can be a vertebrate, preferably a mammal, and more preferably a human. The methods comprise detecting and/or quantitating levels and/or extent of MN/CA9 gene expression product(s) in a sample comprising neoplastic cells taken from the RCC/CCC patient, and determining that the patient has a poorer prognosis if the level and/or extent of MN/CA9 gene expression product(s) indicates that 50% or fewer of cells in said sample express MN/CA9 gene expression product. A poorer prognosis can be measured, for example, in terms of shortened cumulative survival, increased risk of recurrence and/or increased risk of metastasis.

In a preferred embodiment of the invention, the MN/CA9 gene expression product is MN/CA IX antigen, and the MN/CA IX antigen is quantitated in vertebrate samples, preferably mammalian samples, more preferably human samples, comprising neoplastic cells. In addition to predicting clinical outcome, the methods of the present invention can also identify high-risk patients in need of adjuvant therapy, and/or identify candidates for MN/CA9/CA IX-targeted therapies, among other courses of treatment.

In one aspect, the invention concerns methods which are prognostic for renal cell carcinoma afflicting a subject vertebrate, wherein an exemplary method comprises:

(a) detecting the presence or absence of MN/CA9 gene expression product in a sample comprising neoplastic cells taken from said vertebrate, (b) if MN/CA9 gene expression product is present in said sample, quantitating the level and/or extent of said MN/CA9 gene expression product relative to the number of cells in said sample, and (c) determining that said subject vertebrate has a poorer prognosis if the level and/or extent of MN/CA9 gene expression product of steps (a) and (b) indicates that 50% or fewer of cells in said sample express MN/CA9 gene expression product;

wherein said MN/CA9 gene expression product is encoded by a nucleotide sequence selected from the group consisting of:

(1) SEQ ID NO: 1's coding region;

(2) nucleotide sequences that hybridize under stringent hybridization conditions of 50% formamide at 42 degree C. to complement of SEQ ID NO: 1's coding region; and (3) nucleotide sequences that differ from SEQ ID NO: 1's coding region or from the nucleotide sequences of (2) in codon sequence due to the degeneracy of the genetic code. SEQ ID NO: 1 is the full-length MN cDNA as disclosed in Zavada et al. WO 95/34650, supra.

Preferred assays to be used according to the methods of the invention to detect said MN/CA9 gene expression product in detecting step (a) are those wherein said MN/CA9 gene expression product comprises an MN/CA IX protein or MN/CA IX polypeptide, and said assays are selected from the group consisting of Western blots, enzyme-linked immunosorbent assays, radioimmunoassays, competition immunoassays, dual antibody sandwich assays, immunohistochemical staining assays, agglutination assays, and fluorescent immunoassays. More preferably, said MN/CA9 gene expression product detecting step (a) comprises the use of immunohistochemical staining, and said quantitating step (b) comprises determining the percentage of MN/CA IX immunoreactive cells and/or the intensity and/or extent of immunostaining of MN/CA IX immunoreactive cells, wherein if 50% or fewer cells in said sample are immunoreactive, concluding that said vertebrate has a poorer prognosis than if more than 50% of cells in said sample are immunoreactive. Preferably, the quantitating step (b) comprises determining the percentage of MN/CA IX immunoreactive cells. Still more preferably, said detecting step (a) comprises the use of a MN/CA IX-specific monoclonal antibody, preferably the M75 MAb secreted by the hybridoma VU-M75 which has Accession No. ATCC HB 11128.

In a preferred embodiment of the invention, the MN/CA9 gene expression product is CA IX antigen, and the CA IX antigen is quantitated in preneoplastic/neoplastic vertebrate samples, preferably mammalian samples, more preferably human samples, wherein the vertebrate, mammal or human is afflicted with RCC, particularly CCC. Such samples can be, for example, tissue specimens, tissue extracts, body fluids, cells, cell lysates and cell extracts, among other samples. Preferred tissue specimens to assay by immunohistochemical staining, for example, include cell smears, histological sections from biopsied tissues or organs, and imprint preparations among other tissue samples. Such tissue specimens can be variously maintained, for example, they can be fresh, frozen, or formalin-, alcohol- or acetone- or otherwise fixed and/or paraffin-embedded and deparaffinized. Preferred tissue samples are formalin-fixed, paraffin-embedded tissue samples.

An exemplary and preferred method which is prognostic for renal cell carcinoma afflicting a subject vertebrate comprises:

(a) detecting the presence or absence of MN/CA9 gene expression product in a sample comprising neoplastic cells taken from said vertebrate, said detecting comprising the use of immunohistochemical staining with MN/CA IX-specific antibody to detect the presence or absence of MN/CA IX protein in the sample;

(b) if MN/CA IX protein is present in said sample, quantitating the level and/or extent of said MN/CA IX protein in said sample relative to the number of cells, comprising determining a MN/CA IX immunoreactivity score of cells in said sample, comprising determining the percentage of immunoreactive cells with cell membrane staining, wherein the percentage of immunoreactive cells is assigned an immunoreactivity score with a value of 0 if no immunoreactive cells,
a value of 1 if 50% or less immunoreactive cells, or
a value of 2 if more than 50% immunoreactive cells; and wherein if the immunoreactivity score of the sample is 1 or less, concluding in step (c) that said vertebrate has a poorer prognosis than if said immunoreactivity score is 2.

In an alternative preferred embodiment, preferred assays to be used according to the methods of the invention in said MN/CA9 gene expression product detecting step (a) are nucleic acid-based assays, wherein said MN/CA9 gene expression product comprises a mRNA encoding an MN/CA IX protein or MN/CA IX polypeptide, or a cDNA complementary to mRNA encoding an MN/CA IX protein or MN/CA IX polypeptide. Preferably, said detecting step (a) is by in situ hybridization, Northern blotting, PCR, RT-PCR, real-time PCR, or by quantitative real-time RT-PCR.

Preferably, the renal cell carcinoma to be tested according to the prognostic methods of the invention for MN/CA9 gene expression product, is selected from the group consisting of renal clear cell carcinoma, papillary cell carcinoma and chromophobe carcinoma. More preferably, the renal cell carcinoma is renal clear cell carcinoma. Preferably said vertebrate is a mammal, more preferably human. Still more preferably, the vertebrate is a human patient, and said renal cell carcinoma is selected from the group consisting of renal clear cell carcinoma, papillary cell carcinoma and chromophobe carcinoma. Preferably, said renal cell carcinoma is a renal clear cell carcinoma tumor, and said sample is taken from said tumor and/or from a metastatic lesion derived from said tumor.

Preferred prognostic methods according to the invention are those wherein a poorer prognosis is measured in terms of shortened cumulative survival, increased risk of recurrence of said renal cell carcinoma and/or increased risk of metastasis. Further preferred methods are those wherein said renal cell carcinoma comprises a tumor or a tumor and one or more metastatic lesions derived from the tumor, and wherein a poorer prognosis is measured in terms of shortened cumulative survival, increased risk of recurrence of said neoplastic disease and/or increased risk of metastasis following surgical removal of the tumor, or the tumor and said one or more metastatic lesions.

Preferably, said prognostic method is used as an aid in the selection of treatment for said renal cell carcinoma afflicting said vertebrate. The methods of the invention can be used, for example, to identify those subsets of patients with the lowest survival rates in order to establish more aggressive therapy regimens. In one embodiment of the invention, detection and quantitation of MN/CA9 gene expression products are used in combination with conventional tumor stage and grade information to determine patient prognosis. For example, if said renal cell carcinoma in said vertebrate has a T-stage of 3 or higher and/or a Fuhrman grade of 3 or higher, then if the detecting step (a) and the quantitating step (b) indicate that 50% or less of cells in said vertebrate sample express MN/CA9 gene expression product, said vertebrate should be treated with more aggressive therapy regimens.

Even if the tumor T-stage is 3 or higher and/or the Fuhrman grade is 3 or higher in said vertebrate, if more than 50% of cells in said sample express MN/CA9 gene expression product, said vertebrate has a better prognosis than if 50% or less of cells in said sample express MN/CA9 gene expression product, and less aggressive therapies should be selected.

Conversely, even if the tumor T-stage is 2 or lower and/or the Fuhrman grade is 2 or lower in said vertebrate, if 50% or less of cells in said sample express MN/CA9 gene expression product, said vertebrate has a worse prognosis than if more than 50% of cells in said sample express MN/CA9 gene expression product, and more aggressive therapies should be selected.

Aspects of the instant invention disclosed herein are described in more detail below.

REFERENCES

1. Novick, A. J. and Campbell, S. C., *Renal tumors; in Walsh, P., editor, Campell's Urology*, Philadelphia: Saunders, pp. 2672-2731 (2002).
2. Jemal et al., "Cancer Statistics," *CA Cancer J. Clin.* 54(1): 8-29 (2004).
3. Chow et al., "Rising incidence of renal cell cancer in the United States," *JAMA*, 281: 1628-1631 (1999).
4. Rioux-Leclercq et al., "Value of immunohistochemical Ki-67 and p53 determinations as predictive factors of outcome in renal cell carcinoma," *Urology.* 55(4): 501-505 (2000).
5. Tsui et al., "Prognostic indicators for renal cell carcinoma: a multivariate analysis of 643 patients using the revised 1997 TNM staging criteria," *J Urol,* 163(4):1090-1095 (2000).
6. Bui et al., "Prognostic factors and molecular markers for renal cell carcinoma," *Expert Rev Anticancer Ther.* 1(4): 565-575 (2001).
7. Ivanov et al., "Expression of hypoxia-inducible cell-surface transmembrane carbonic anhydrases in human cancer," *Am. J. Pathol.,* 158: 905-919 (2001).
8. Zavada et al., "Expression of MaTu-MN protein in human tumor cultures and in clinical specimens," *Int. J. Cancer,* 54: 268-274 (1993).
9. Oosterwijk et al., "Monoclonal antibody G250 recognizes a determinant present in renal cell carcinoma and absent from normal kidney," *Int. J. Cancer,* 38: 489-494 (1986).
10. Murakami et al., "CA9 gene expression as a potential biomarker in renal cell carcinoma," *BJU Int.,* 83: 743-747 (1999).
11. Uemura et al., "MN/CA IX/G250 as a potential target for immunotherapy of renal cell carcinomas," *Br. J. Cancer,* 81: 741-746 (1999).
12. Liao et al., "Identification of the MN/CA IX protein as a reliable diagnostic biomarker of clear cell carcinoma of the kidney," *Cancer Res.,* 57: 2827-2831 (1997).
13. Fuhrman et al., "Prognostic significance of morphologic parameters in renal cell carcinoma," *Am J. Surg Pathol.* 6: 655-663 (1982).
14. Pastorekova et al., "A novel quasi-viral agent, MaTu, is a two-component system," *Virology,* 187: 620-626 (1992).
15. Bui et al., "Carbonic Anhydrase IX Is an Independent Predictor of Survival in Advanced Renal Clear Cell Carcinoma: Implications for Prognosis and Therapy," *Clin Cancer Res,* 9(2): 802-811 (2003).
16. Liao et al., "Identification of the MN antigen as a diagnostic biomarker of cervical intraepithelial squamous and glandular neoplasia and cervical carcinomas," *Am. J. Pathol.* 145: 598-609 (1994).
17. Bui et al., "Prognostic value of carbonic anhydrase IX and Ki67 as predictors of survival for renal clear cell carcinoma," *J. Urol.* 171: 2461-2466 (2004).
18. Zavada et al., "Soluble form of carbonic anhydrase IX (CA IX) in the serum and urine of renal carcinoma patients," *Br. J. Cancer.* 89: 1067-1071 (2003).
19. Jocham et al, "Adjuvant autologous renal tumor cell vaccine and risk of tumour progression in patients with renal-cell carcinoma after radical nephrectomy: Phase III, randomized controlled trial," *Lancet,* 363: 594-599 (2004).
20. Divgi et al., "Phase I/II radioimmunotherapy trial with iodine-131-labeled monoclonal antibody G250 in metastatic renal cell carcinoma," *Clin. Cancer Res.* 4: 2729-2739 (1998).
21. Tso et al., "Induction of G250-targeted and T-cell mediated antitumor activity against renal cell carcinoma using a chimeric fusion protein consisting of G250 and granulocyte/monocyte-colony stimulating factor," *Cancer Res.* 61: 7925-7933 (2001).
22. Opavsky et al. "Human MN/CA9 gene, a novel member of the carbonic anhydrase family: structure and exon to protein domain relationships," *Genomics.* 33: 480-487 (1996).
23. Uemura et al., "Expression of Tumor-Associated Antigen MN/G250 in Urologic Carcinoma: Potential Therapeutic Target," *J. Urol.* 157 (4 Suppl.): 377 (Abstract 1475; 1997).
24. Parkkila and Parkkila, "Carbonic anhydrase in the alimentary tract. Roles of the different isozymes and salivary factors in the maintenance of optimal conditions in the gastrointestinal canal," *Scand J Gastroenterol.,* 31: 305-317 (1996).
25. Potter and Harris, "Diagnostic, prognostic and therapeutic implications of carbonic anhydrases in cancer," *Br J Cancer.* 89: 2-7 (2003).
26. Wingo et al., "The catalytic properties of human carbonic anhydrase IX," *Biochem Biophys Res Commun.* 288: 666-669 (2001).
27. Pastorek et al., "Cloning and characterization of MN, a human tumor-associated protein with a domain homologous to carbonic anhydrase and a putative helix-loop-helix DNA binding segment," *Oncogene.* 9: 2877-2888 (1994).
28. Saarnio et al., "Immunohistochemical study of colorectal tumors for expression of a novel transmembrane carbonic anhydrase, MN/CA IX, with potential value as a marker of cell proliferation," *Am J Pathol,* 153: 279-285 (1998).
29. Svastova et al., "Carbonic anhydrase IX reduces E-cadherin-mediated adhesion of MDCK cells via interaction with β-catenin," *Exp Cell Res,* 290:332-345 (2003).
30. Wykoff et al. "Hypoxia-inducible expression of tumor-associated carbonic anhydrases," *Cancer Res.* 60: 7075-7083 (2000).
31. Ivanov et al., "Down-regulation of transmembrane carbonic anhydrases in renal cell carcinoma cell lines by wild-type von Hippel-Lindau transgenes," *Proc Natl Acad Sci (USA),* 95:12596-12601 (1998).
32. Maxwell et al., "The tumour suppressor protein VHL targets hypoxia-inducible factors for oxygen-dependent proteolysis," *Nature,* 399: 271-275 (1999).
33. Jaakkola et al. "Targeting of HIFα to the von Hippel Lindau ubiquitination complex by $O_2$-regulated prolyl hydroxylation," *Science.* 292:468-472 (2001).
34. Koukourakis et al., "Hypoxia-regulated carbonic anhydrase-9 (CA9) relates to poor vascularization and resistance of squamous cell head and neck cancer to chemoradiotherapy," *Clin Cancer Res.* 7: 3399-3403 (2001).
35. Giatromanolaki et al. "Expression of hypoxia-inducible carbonic anhydrase-9 relates to angiogenic pathways and independently to poor outcome in non-small cell lung cancer," *Cancer Res,* 61:7992-7998 (2001).
36. Swinson et al., "Carbonic anhydrase IX expression, a novel surrogate marker of tumor hypoxia is associated with a poor prognosis in non-small cell lung cancer," *J Clin Oncol,* 21: 473-482 (2003).

37. Chia et al., "Prognostic significance of a novel hypoxia-regulated marker, carbonic anhydrase IX, in invasive breast carcinoma," *J Clin Oncol*, 19: 3660-3668 (2001).
38. Loncaster et al., "Carbonic anhydrase expression, a potential new intrinsic marker of hypoxia: correlations with tumor oxygen measurements and prognosis in locally advanced carcinoma of the cervix," *Cancer Res.* 61:6394-6399 (2001).
39. Liao and Stanbridge, "Expression of the MN Antigen in Cervical Papanicolaou Smears Is an Early Diagnostic Biomarker of Cervical Dysplasia," *Cancer Epidemiology. Biomarkers & Prevention*, 5: 549-557 (1996);
40. Brewer et al., "A Study of Biomarkers in Cervical Carcinoma and Clinical Correlation of the Novel Biomarker MN," *Gynecologic Oncology* 63: 337-344 (1996).
41. McKiernan et al., "Expression of the Tumor-associated Gene MN: A Potential Biomarker for Human Renal Cell Carcinoma," *Cancer Res.* 57: 2362-2365 (1997).
42. Pastorekova and Zavada, "Carbonic anhydrase IX (CA IX) as a potential target for cancer therapy," *Cancer Therapy* 2: 245-262 (2004).
43. Pastorekova et al., "Carbonic Anhydrase IX: Analysis of stomach complementary DNA sequence and expression in human and rat alimentary tracts," *Gastroenterology*, 112: 398-408 (1997).
44. Leppilampi et al., "Carbonic anhydrase isozymes IX and XII in gastric tumors," *World J Gastroenterol*, 9: 1398-1403 (2003).
45. Glennie et al., "Univalent antibodies kill tumour cells in vitro and in vivo," *Nature.* 295(5851): 712-714 (Feb. 25, 1982).
46. Dalbadie-McFarland et al., "Oligonucleotide-directed mutagenesis as a general and powerful method for studies of protein function," *PNAS* (USA), 79(21): 6409-6413 (Nov. 1982).
47. Hunter, W. M., "Radioimmunoassay," *In: Handbook of Experimental Immunology*, pp. 14.1-14.40 (D. W. Weir ed.; Blackwell, Oxford/London/Edinburgh/Melbourne; 1978).
48. Brown, J. M., "Exploiting the hypoxic cancer cell: mechanisms and therapeutic strategies," *Molecular Medicine Today.* 6: 157-162 (April 2000).
49. Trinh et al., "Enzyme/prodrug gene therapy: comparison of cytosine deaminase/5-fluorocytosine versus thymidine kinase/ganciclovir enzyme/prodrug systems in a human colorectal carcinoma cell line," *Cancer Res.*, 55: 4808-4812 (1995).

ABBREVIATIONS

The following abbreviations are used herein:

| | |
|---|---|
| aa | amino acid |
| AEC | 3-amino-9-ethylcarbazole |
| ATCC | American Type Culture Collection |
| bp | base pairs |
| CA | carbonic anhydrase |
| CAI | carbonic anhydrase inhibitor |
| CCC | clear cell subtype of renal cell carcinoma |
| Ci | curie |
| CI | confidence interval |
| cm | centimeter |
| CS | cumulative survival |
| C-terminus | carboxyl-terminus |
| °C. | degrees centigrade |
| DAB | diaminobenzidine tetrahydrochloride |
| ds | double-stranded |
| EDTA | ethylenediaminetetraacetate |
| ELISA | enzyme-linked immunosorbent assay |
| Gr | Grade |
| HRP | horseradish peroxidase |
| IC | intracellular |
| IFN | interferon (exemplary cytokine) |
| IL-2 | interleukin-2 (exemplary cytokine) |
| kb | kilobase |
| kbp | kilobase pairs |
| kd or kDa | kilodaltons |
| M | molar |
| MAb | monoclonal antibody |
| min. | minute(s) |
| mg | milligram |
| ml | milliliter |
| mM | millimolar |
| mmol | millimole |
| n | number of cases |
| ng | nanogram |
| nm | nanometer |
| nM | nanomolar |
| nt | nucleotide |
| N-terminus | amino terminus |
| OR | odds ratio |
| ORF | open reading frame |
| PBS | phosphate buffered saline |
| PCR | polymerase chain reaction |
| PG | proteoglycan |
| pI | isoelectric point |
| RCC | renal cell carcinoma |
| RT-PCR | reverse transcription polymerase chain reaction |
| RTU | ready to use |
| SD | standard deviation |
| SDS | sodium dodecyl sulfate |
| SPSS | "Statistical Package for the Social Sciences" |
| SSPE | NaCl (0.18 M), sodium phosphate (0.01 M), EDTA (0.001 M) |
| Stg | stage |
| TM | transmembrane |
| Tris | tris (hydroxymethyl) aminomethane |
| μCi | microcurie |
| μg | microgram |
| μl | microliter |
| μM | micromolar |

BRIEF DESCRIPTION OF THE FIGURES

FIG. 1 shows a high pattern of MN/CA IX staining in renal papillary carcinoma [MN/CA IX×100].

FIG. 2 shows intensive membraneous staining seen in renal clear cell carcinoma (CCC) [MN/CA IX×200].

FIG. 3 graphically shows cumulative survival (CS) of 61 CCC patients according to T stage (a), tumor grade (b), and MN/CA IX expression (c).

FIG. 4 graphically shows CS of 61 CCC patients according to T stage and MN/CA IX expression.

FIG. 5 graphically shows CS of 61 CCC patients according to tumor grade and MN/CA IX expression.

NUCLEOTIDE AND AMINO ACID SEQUENCE SYMBOLS

The following symbols are used to represent nucleotides herein:

| Base Symbol | Meaning |
|---|---|
| A | adenine |
| C | cytosine |
| G | guanine |
| T | thymine |

-continued

| Base Symbol | Meaning |
|---|---|
| U | uracil |
| I | inosine |
| M | A or C |
| R | A or G |
| W | A or T/U |
| S | C or G |
| Y | C or T/U |
| K | G or T/U |
| V | A or C or G |
| H | A or C or T/U |
| D | A or G or T/U |
| B | C or G or T/U |
| N/X | A or C or G or T/U |

There are twenty main amino acids, each of which is specified by a different arrangement of three adjacent nucleotides (triplet code or codon), and which are linked together in a specific order to form a characteristic protein. A three-letter or one-letter convention may be used herein to identify said amino acids as follows:

| Amino acid name | 3 Ltr. Abbrev. | 1 Ltr. Abbrev. |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Unknown or other |  | X |

DETAILED DESCRIPTION

The invention provides methods for prognosis of renal cell carcinoma (RCC) in a patient, particularly for renal clear cell carcinoma (CCC). The methods include quantifying the level and/or extent of MN/CA9 gene expression product, if any, present in a sample taken from a patient that has been diagnosed with renal cell carcinoma, particularly CCC. The MN/CA9 gene expression product can be CA IX protein, CA IX polypeptide, CA9 nucleic acids, particularly mRNA encoding a CA IX protein or polypeptide, a cDNA corresponding to an mRNA encoding a CA IX protein or polypeptide, or the like. The MN/CA9 gene expression product levels are quantified relative to the number of the cells in the sample, comprising determining the percentage of cells that are expressing MN/CA9, and said levels, including absence of MN/CA IX, are correlated with a better or worse prognosis for the patient. Said MN/CA9 gene expression product is preferably a CA IX protein or CA IX polypeptide quantitated in a sample taken from the patient. The methods can be used, for example, to aid in the selection of therapies, and to monitor cancer chemotherapy, tumor reappearance and metastasis. In particular, the levels of MN/CA9 gene expression products can be used to identify high risk patients in need of adjuvant therapies, particularly those in need of more aggressive therapies from the outset.

A preferred method of quantifying the level and/or extent of MN/CA9 gene expression product in a patient sample is by immunohistochemical staining. More preferably, said MN/CA9 gene expression product detecting step (a) is by immunohistochemical staining, and said quantitating step (b) comprises determining the percentage of immunoreactive cells and/or the intensity or extent of immunostaining of immunoreactive cells. Still more preferably, said detecting step (a) comprises the use of a MN/CA IX-specific monoclonal antibody, preferably the M75 MAb secreted by the hybridoma VU-M75 which has Accession No. ATCC HB 11128 and has been deposited under the Budapest Treaty at the American Type Culture Collection.

In an alternative preferred embodiment, preferred assays to be used according to the methods of the invention in said MN/CA9 gene expression product detecting and quantitating steps (a) and (b) are nucleic acid-based assays, wherein said MN/CA9 gene expression product comprises a mRNA encoding a MN/CA IX protein or MN/CA IX polypeptide, or a cDNA complementary to mRNA encoding an MN/CA IX protein or MN/CA IX polypeptide. Preferably, said detecting and quantitating steps (a) and (b) are by in situ hybridization or by Northern blotting.

Suitable detection means include the use of labels such as radionuclides, enzymes, coenzymes, fluorescers, chemiluminescers, chromogens, enzyme substrates or co-factors, enzyme inhibitors, free radicals, particles, dyes and the like. Such labeled reagents may be used in a variety of well known assays, such as radioimmunoassays, enzyme immunoassays, e.g., ELISA, fluorescent immunoassays, and the like. See for example, U.S. Pat. Nos. 3,766,162; 3,791,932; 3,817,837; and 4,233,402.

In certain embodiments of the invention, the percentage of cells in a sample that are expressing mRNA or cDNA that encodes a CA IX protein or a CA IX polypeptide is determined, and thereby correlated with a prognosis for a patient. Where expression of MN/CA9 mRNA or MN/CA9 cDNA is measured, CA9 mRNA or CA9 cDNA expression in 50% or less of cells in the sample is indicative of poorer prognosis.

Additionally, methods can be used in combination; for example, both CA IX protein and CA9 mRNA expression can be assessed by immunohistochemistry and in situ hybridization, respectively. A preferred embodiment would be exemplified by screening tumor samples from patients with renal cell carcinoma and matched samples of non-neoplastic renal tissues as a control. One of ordinary skill in the art using routine methods could optimize the assays of this invention to determine where the 50% cutoff would be, or how the 50% cutoff could be determined for different types of tissue samples for patients with renal cell carcinoma, particularly renal clear cell carcinoma.

It can be appreciated by those of skill in the art that various other preneoplastic/neoplastic samples can be used to quantify the MN/CA9 gene expression products. For example, in the case of a patient afflicted with a renal cell carcinoma, the sample may be taken from the tumor or from a metastatic lesion derived from the tumor, or from the extracellular fluid within or immediately surrounding the tumor or metastatic lesion.

It can further be appreciated that alternate methods, in addition to those disclosed herein, can be used to detect and quantify the MN/CA9 gene expression products.

Neoplastic Cells/Tissues

As used herein, "cancerous" and "neoplastic" have equivalent meanings, as well as "precancerous" and preneoplastic".

As used herein, "renal cell carcinoma" or "RCC" is considered to be a carcinoma of the renal parenchyma, and is also called renal cancer, adenocarcinoma of the kidney, renal adenocarcinoma, hypernephroid carcinoma, hypernephroma, or Grawitz's tumor. Renal clear cell carcinoma or "CCC" is the predominant subtype of renal cell carcinoma comprising up to about 85% of RCCs. The other 3 subtypes of RCC are the granular cell, mixed granular and clear cell, and spindle cell subtypes.

In a preferred embodiment of the invention, the MN/CA9 gene expression product is MN/CA IX antigen, and the MN/CA IX antigen is detected and quantitated in vertebrate samples, preferably mammalian samples, more preferably human samples, comprising neoplastic cells. Such samples can be tissue specimens, tissue extracts, body fluids, cells, cell lysates and cell extracts, among other samples. Preferred tissue specimens to assay by immunohistochemical staining, for example, include cell smears, histological sections from biopsied tissues or organs, and imprint preparations among other tissue samples. An exemplary immunohistochemical staining protocol is described below in the Materials and Methods section of Example 1. Such tissue specimens can be variously maintained; for example, they can be fresh, frozen, or formalin-, alcohol- or acetone- or otherwise fixed and/or paraffin-embedded and deparaffinized. Biopsied tissue samples can be, for example, those samples removed by aspiration, bite, brush, cone, chorionic villus, endoscopic, excisional, incisional, needle, fine needle, percutaneous punch, and surface biopsies, among other biopsy techniques. Preferred tissue samples are formalin-fixed, paraffin-embedded tissue samples.

Assays

Many formats can be adapted for use with the methods of the present invention. The detection and quantitation of CA IX protein or CA IX polypeptide can be performed, for example, by Western blots, enzyme-linked immunosorbent assays, radioimmunoassays, competition immunoassays, dual antibody sandwich assays, immunohistochemical staining assays, agglutination assays, fluorescent immunoassays, immunoelectron and scanning microscopy using immunogold, among other assays commonly known in the art. The quantitation of MN/CA9 gene expression products in such assays can be adapted by conventional methods known in the art; for example, if the detection method is by immunohistochemical staining, the quantitation of CA IX protein or CA IX polypeptide can be performed by determining the percentage of immunoreactive cells and/or the intensity or extent of immunostaining of immunoreactive cells, and can additionally comprise addition or multiplication of these values, or other mathematical calculations using these values.

It is also apparent to one skilled in the art of immunoassays that antibodies to MN/CA IX proteins or polypeptides can be used to detect and quantitate MN/CA IX antigen in body tissues and/or cells of patients. In one embodiment, an immunometric assay may be used in which a labelled antibody made to a MN/CA IX protein or polypeptide comprising the extracellular domain is used. In such an assay, the amount of labelled antibody which complexes with the antigen-bound antibody is directly proportional to the amount of CA IX antigen in the sample.

The monoclonal antibodies useful according to this invention to identify MN/CA IX proteins/polypeptides can be labeled in any conventional manner, for example, with enzymes such as horseradish peroxidase (HRP), fluorescent compounds, or with radioactive isotopes such as, $^{125}$I, among other labels. A preferred label, according to this invention is $^{125}$I, and a preferred method of labeling the antibodies is by using chloramine-T [47]. Also preferred is the method of labeling the antibodies using peroxidase. Many other means of visualizing the MN/CA9 gene expression products known to those of skill in the art can also be used.

Exemplary Immunohistochemical Assays

An exemplary immunohistochemical assay described in Example 1 below uses antibody staining to investigate the distribution and expression pattern of MN/CA IX. Paraffin-embedded tissue sections from nephrectomy patients are deparaffinized and rehydrated, then stained with the MN/CA IX-specific monoclonal antibody M75. The sections are then reacted with a biotinylated antibody recognizing mouse IgG, and subsequently with streptavidin-peroxidase conjugate. The immunoperoxidase complexes are then visualized with a chromogen, such as diaminobenzidine tetrahydrochloride (DAB) or 3-amino-9-ethyl carbazole (AEC).

Nucleic Acid-Based Assays

In certain embodiments of the invention, mRNA or cDNA that encodes a CA IX protein or a CA IX polypeptide is detected and if present, the percentage of cells in a sample that are expressing CA9 mRNA or cDNA is determined, and thereby correlated with a prognosis for a patient. An exemplary nucleic acid-based method is Northern blotting, where the nucleic acid sequence used as a probe for detecting MN/CA9-specific mRNA expression is complementary to all or part of the MN/CA9 cDNA sequence. A preparation of RNA is run on a denaturing agarose gel, and transferred to a suitable support, such as activated cellulose, nitrocellulose or glass or nylon membranes. The nucleic acids used to detect the MN/CA9 mRNA or cDNA may be radiolabelled and analyzed by autoradiography. Non-radioactive labels, for example, such as fluorophores or reporter groups such as digoxigenin may also be used to detect the MN/CA9 mRNA or cDNA.

An alternate preferred method for measuring CA IX-specific mRNA expression is the detection of CA9 mRNA expression via hybridization of a nucleic acid probe derived from MN/CA9 cDNA sequence to RT-PCR products generated from RNA isolated from a biological sample. Exemplary PCR primers designed to amplify a 240 bp cDNA fragment of the CA9 gene are sense 5'-AGGAGGATCTGCC CAGTGA-3' [SEQ ID NO: 10]; antisense 5'-GCCAATGACTCTGGT-CATC-3') [SEQ ID NO: 11.] Murakami et al. and Uemura et al. have reported that CA IX detection by RT-PCR in patient samples correlate well with immunohistochemistry [10, 11].

MN Gene and Protein

The terms "MN/CA IX" and "MN/CA9" are herein considered to be synonyms for MN. Also, the G250 antigen is considered to refer to MN protein/polypeptide [23].

Zavada et al., WO 93/18152 and/or WO 95/34650 disclose the MN cDNA sequence [SEQ ID NO: 1], the MN amino acid sequence [SEQ ID NO: 2], and the MN genomic sequence [SEQ ID NO: 3]. The MN gene is organized into 11 exons and 10 introns.

The ORF of the MN cDNA [SEQ ID NO: 1] has the coding capacity for a 459 amino acid protein with a calculated molecular weight of 49.7 kd. The overall amino acid composition of the MN/CA IX protein is rather acidic, and predicted to have a pI of 4.3. Analysis of native MN/CA IX protein from CGL3 cells by two-dimensional electrophoresis followed by immunoblotting has shown that in agreement with computer prediction, the MN/CA IX is an acidic protein existing in several isoelectric forms with pIs ranging from 4.7 to 6.3. [CGL3 cells are hybrid HeLa fibroblast cells that are tumorigenic, derived from HeLa D98/AH.2 (also known as HeLa S), a mutant HeLa clone that is hypoxanthine guanine phosphoribosyl transferase-deficient (HGPRT⁻) reported in Stanbridge et al., *Science*. 215: 252-259 (15 Jan. 1982).]

The first thirty seven amino acids of the MN protein is the putative MN signal peptide [SEQ ID NO: 6]. The MN protein has an extracellular domain [amino acids (aa) 38414; SEQ ID NO: 7], a transmembrane domain [aa 415-434; SEQ ID NO: 8] and an intracellular domain [aa 435-459; SEQ ID NO: 9]. The extracellular domain contains the proteoglycan-like domain [aa 53-111: SEQ ID NO: 4] and the carbonic anhydrase (CA) domain [aa 135-391; SEQ ID NO: 5].

The CA domain is essential for induction of anchorage independence, whereas the TM anchor and IC tail are dispensable for that biological effect. The MN protein is also capable of causing plasma membrane ruffling in the transfected cells and appears to participate in their attachment to the solid support. The data evince the involvement of MN in the regulation of cell proliferation, adhesion and intercellular communication.

MN Proteins and Polypeptides

The phrase "MN proteins and/or polypeptides" (MN proteins/polypeptides) is herein defined to mean proteins and/or polypeptides encoded by an MN gene or fragments thereof. An exemplary and preferred MN protein according to this invention has the deduced amino acid sequence represented by SEQ ID NO: 2. Preferred MN proteins/polypeptides are those proteins and/or polypeptides that have substantial homology with the MN protein [SEQ ID NO: 2]. For example, such substantially homologous MN proteins/polypeptides are those that are reactive with MN-specific antibodies, preferably the Mab M75 or its equivalent. The VU-M75 hybridoma that secretes the M75 Mab was deposited at the ATCC under HB 11128 on Sep. 17, 1992.

A "polypeptide" or "peptide" is a chain of amino acids covalently bound by peptide linkages and is herein considered to be composed of 50 or less amino acids. A "protein" is herein defined to be a polypeptide composed of more than 50 amino acids. The term polypeptide encompasses the terms peptide and oligopeptide.

As used herein, "low CA IX" or "low MN/CA IX" refers to a determination that 50% or less of cells in a neoplastic sample taken from an RCC patient express the MN/CA9 gene. Correspondingly, "high CA IX" or "high MN/CA IX" refers to a determination that more than 50% of cells in a neoplastic sample taken from an RCC patient express the MN/CA9 gene.

It can be appreciated that a protein or polypeptide produced by a neoplastic cell in vivo could be altered in sequence from that produced by a tumor cell in cell culture or by a transformed cell. Thus, MN proteins and/or polypeptides which have varying amino acid sequences including without limitation, amino acid substitutions, extensions, deletions, truncations, interpolations and combinations thereof, fall within the contemplated scope of this invention, provided the protein or polypeptide containing them is immunogenic, and antibodies elicited by such a polypeptide or protein cross-react with naturally occurring MN proteins and polypeptides to a sufficient extent to provide protective immunity and/or anti-tumorigenic activity when administered as a vaccine. It can also be appreciated that a protein extant within body fluids is subject to degradative processes, such as, proteolytic processes; thus, MN proteins that are significantly truncated and MN polypeptides may be found in body fluids, such as, sera. The phrase "MN antigen" is used herein to encompass MN proteins and/or polypeptides.

It will further be appreciated that the amino acid sequence of MN proteins and polypeptides can be modified by genetic techniques. One or more amino acids can be deleted or substituted. Such amino acid changes may not cause any measurable change in the biological activity of the protein or polypeptide and result in proteins or polypeptides which are within the scope of this invention, as well as, MN muteins.

Nucleic Acid Probes

Nucleic acid probes of this invention are those comprising sequences that are complementary or substantially complementary to the MN cDNA sequence [SEQ ID NO: 1] or to other MN gene sequences, such as, the complete genomic sequence [SEQ ID NO: 3]. The phrase "substantially complementary" is defined herein to have the meaning as it is well understood in the art and, thus, used in the context of standard hybridization conditions. The stringency of hybridization conditions can be adjusted to control the precision of complementarity. Two nucleic acids are, for example, substantially complementary to each other, if they hybridize to each other under stringent hybridization conditions.

Stringent Hybridization Conditions

Stringent hybridization conditions are considered herein to conform to standard hybridization conditions understood in the art to be stringent. Only very closely related nt sequences having a homology of at least 80-90% would hybridize to each other under stringent hybridization conditions.

For example, it is generally understood that stringent conditions encompass relatively low salt and/or high temperature conditions, such as provided by 0.02 M to 0.15 M NaCl at temperatures of 50° C. to 70° C. such as, 0.15 M to 0.9 M salt at temperatures ranging from 20° C. to 55° C. Less stringent conditions can be made more stringent by adding increasing amounts of formamide, which serves to destabilize hybrid duplexes as does increased temperature, such as provided by 0.15 M to 0.9 M NaCl in the presence of 50% formamide at 42° C. with a final wash of 0.1% SSPE and 0.1% SDS at 65° C.

Exemplary stringent hybridization conditions are described in Sambrook et al., *Molecular Cloning: A Laboratory Manual*, pages 1.91 and 9.47-9.51 (Second Edition, Cold Spring Harbor Laboratory Press; Cold Spring Harbor, N.Y.; 1989); Maniatis et al., *Molecular Cloning: A Laboratory Manual*, pages 387-389 (Cold Spring Harbor Laboratory; Cold Spring Harbor, N.Y.; 1982); Tsuchiya et al., *Oral Surgery. Oral Medicine, Oral Pathology*. 71(6): 721-725 (June 1991); and in U.S. Pat. No. 5,989,838, U.S. Pat. No. 5,972,353, U.S. Pat. No. 5,981,711, and U.S. Pat. No. 6,051,226.

Antibodies

The term "antibodies" is defined herein to include not only whole antibodies but also biologically active fragments of antibodies, preferably fragments containing the antigen binding regions. Further included in the definition of antibodies are bispecific antibodies that are specific for MN protein and to another tissue-specific antigen.

Antibodies useful according to the methods of the invention may be prepared by conventional methodology and/or by genetic engineering. Antibody fragments may be genetically engineered, preferably from the variable regions of the light and/or heavy chains ($V_H$ and $V_L$), including the hypervariable regions, and still more preferably from both the $V_H$ and $V_L$ regions. For example, the term "antibodies" as used herein includes polyclonal and monoclonal antibodies and biologically active fragments thereof including among other possibilities "univalent" antibodies [45]; Fab proteins including Fab' and F(ab)$_2$ fragments whether covalently or non-covalently aggregated; light or heavy chains alone, preferably variable heavy and light chain regions ($V_H$ and $V_L$ regions), and more preferably including the hypervariable regions [otherwise known as the complementarity determining regions (CDRs) of the $V_H$ and $V_L$ regions]; F$_c$ proteins; "hybrid" antibodies capable of binding more than one antigen; constant-variable region chimeras; "composite" immunoglobulins with heavy and light chains of different origins; bispecific antibodies, preferably bispecific MAbs; "altered" antibodies with improved specificity and other characteristics as prepared by standard recombinant techniques and also oligonucleotide-directed mutagenesis techniques [46].

The antibodies useful according to this invention to identify CA IX proteins/polypeptides can be labeled in any conventional manner, for example, with enzymes such as horseradish peroxidase (HRP), fluorescent compounds, or with radioactive isotopes such as, $^{125}$I, among other labels. A preferred label, according to this invention is $^{125}$I, and a preferred method of labeling the antibodies is by using chloramine-T [47].

Representative monoclonal antibodies useful according to this invention include Mabs M75, MN9, MN12 and MN7 described in earlier Zavada et al. patents and patent applications. [U.S. Pat. No. 6,297,041; U.S. Pat. No. 6,204,370; U.S. Pat. No. 6,093,548; U.S. Pat. No. 6,051,226; U.S. Pat. No. 6,004,535; U.S. Pat. No. 5,989,838; U.S. Pat. No. 5,981,711; U.S. Pat. No. 5,972,353; U.S. Pat. No. 5,955,075; U.S. Pat. No. 5,387,676; US Application Nos: 20030049828 and 20020137910; and International Publication No. WO 03/100029]. Monoclonal antibodies useful according to this invention serve to identify MN proteins/polypeptides in various laboratory prognostic tests, for example, in clinical samples. For example, monoclonal antibody M75 (Mab M75) is produced by mouse lymphocytic hybridoma VU-M75, which was deposited under ATCC designation HB 11128 on Sep. 17, 1992 at the American Tissue Type Culture Collection [ATCC]. The production of hybridoma VU-M75 is described in Zavada et al., International Publication No. WO 93/18152. Mab M75 recognizes both the nonglycosylated GST-MN fusion protein and native CA IX protein as expressed in CGL3 cells equally well. The M75 Mab recognizes both native and denatured forms of the CA IX protein [14].

General texts describing additional molecular biological techniques useful herein, including the preparation of antibodies include Berger and Kimmel, *Guide to Molecular Cloning Techniques, Methods in Enzymoloqy*, Vol. 152, Academic Press, Inc., Sambrook et al., *Molecular Cloning: A Laboratory Manual*, (Second Edition, Cold Spring Harbor Laboratory Press; Cold Spring Harbor, N.Y.; 1989) Vol. 1-3; *Current Protocols in Molecular Biology*, F. M. Ausabel et al. [Eds.], Current Protocols, a joint venture between Green Publishing Associates, Inc. and John Wiley & Sons, Inc. (supplemented through 2000), Harlow et al., *Monoclonal Antibodies: A Laboratory Manual*, Cold Spring Harbor Laboratory Press (1988), Paul [Ed.]; *Fundamental Immunology*, Lippincott Williams & Wilkins (1998), and Harlow et al., *Using Antibodies: A Laboratory Manual*, Cold Spring Harbor Laboratory Press (1998).

MN/CA IX and Prognosis: Use in RCC Therapy Selection

As low levels of CA IX staining correlated with worse outcome (Example 1), detection and quantitation of CA IX can be used to identify high-risk patients in need of aggressive therapies, including adjuvant immunotherapy and CA9-targeted therapies. Careful patient selection and stratification to various adjuvant immunotherapies may delineate those patients most likely to respond to treatment. Responses to systemic cytokine therapy, for example with IFN or IL-2, among other cytokines, in metastatic RCC have been promising. Preliminary data from Bui et al. [15] suggest a relationship between CA IX and immunotherapy response. Similarly, therapies based on monoclonal antibodies to CA IX or immunotherapy with CA IX-based RCC vaccine [15, 19-21], or CA9-directed gene therapies can also be considered according to CA IX detection and quantitation.

In addition, the prognostic methods of the invention can use CA IX detection and quantitation in combination with conventional markers, such as tumor grade and/or tumor stage. The immunohistochemical analysis disclosed herein revealed that lowest survival rates are seen when there is low CA IX in high grade tumors, and low CA IX in high stage tumors. Such patients would be candidates for more aggressive therapy regimens.

Therapeutic Use of MN-Specific Antibodies: The MN-specific antibodies, monoclonal and/or polyclonal, preferably monoclonal, may be used therapeutically in the treatment of CA9-expressing renal cell carcinoma, either alone or in combination with chemotherapeutic drugs or toxic agents, such as ricin A. Further preferred for therapeutic use would be biologically active antibody fragments. Also preferred MN-specific antibodies for such therapeutic uses would be MN-specific humanized monoclonal antibodies, fully human monoclonal antibodies, and/or bispecific antibodies.

MN-specific antibodies can be administered in a therapeutically effective amount, preferably dispersed in a physiologically acceptable, nontoxic liquid vehicle, to patients afflicted with renal cell carcinoma expressing MN/CA IX. The MN-specific antibody can be given alone or as a carrier of an anti-tumor drug. Among the various antiproliferative, antineoplastic or cytotoxic agents that may be linked to the MN-specific antibodies are antimetabolites, such as the antifolate, methotrexate, or the purine or pyrimidine analogs mercaptopurine and fluorouracil. Others include antibiotics, lectins such as ricin and abrin, toxins such as the subunit of diphtheria toxin, radionuclides such as $^{211}$Astatine and $^{131}$Iodine, radiosensitizers such as misanidazole or neutron sensitizers such as boron containing organics. Such agents may be attached to the antibody by conventional techniques such as glutaraldehyde cross-linking.

MN-specific antibodies can be used to target cytotoxic cells (e.g. human T cells, monocytes or NK cells). Cytotoxic cells can be attached to MN-expressing tumor cells through Fc receptors on the cytotoxic cells, which bind the Fc portion of a MN-specific antibody, or via a bridging antibody of dual specificity, that is, a bispecific antibody specific for MN protein and for the cytotoxic cell.

The cytotoxic cell can be targeted by allowing the bispecific antibody to bind the cell. After targeting, the cells can be administered to the patient. Therapy with targeted cells can be used as an adjunct to surgical therapy, radiation therapy, or chemotherapy.

Anti-Idiotype MN-Specific Antibodies as Tumor Vaccines, and Anti-Anti-Idiotype Antibody Sera as Immunotherapeutic: MN-Specific Anti-Idiotype antibodies have therapeutic utility as a vaccine for neoplastic disease associated with abnormal MN expression. MN-specific anti-anti-idiotype sera also have therapeutic anti-tumor efficacy. Those therapeutic utilities are demonstrated by research done with the MN-specific G250 MAb, and anti-idiotype antibodies thereto (Ab2), and further anti-idiotype sera (Ab3) as demonstrated by the studies described below.

Uemura et al., *Biotherapy* (Japan) 10(3): 241-244 (1996) (English summary) define an anti-idiotype antibody (Ab2) as "an antibody directed against an antigenic determinant located within a variable region of the immunoglobulin molecule. Ab2 mimicking the normal antigen (so-called internal image Ab2) may be used as a surrogate antigen for vaccination to trigger the host's immune system specifically against the nominal antigen."

Uemura et al., id., having previously isolated six internal image murine Ab2s directed against the G250 MAb—NUH31, 51, 71, 82 (IgG1) and NUH44 (IgG2a), explores the application of monoclonal Ab2 as tumor vaccines. Uemura et al. investigated in view of "previous results that RCC tumor-associated-antigen-related idiotype vaccination induced antigen-specific humoral as well as cellular responses, the anti-tumor efficacy of anti-anti-idiotype antibody (Ab3) sera obtained from mice immunized with different internal image Ab2 that . . . mimic the RCC-associated antigen . . . G250 [MN] . . . Nu/nu BALB/c mice carrying small established NU12 human RCC xenografts (G250+, 20 mm$^3$) . . . receiving an s.c. injection of $2\times10^5$ SK-RC-52 (G250+) RCC cells were treated by i.p. injection of 0.2 ml Ab3 sera. This treatment resulted in complete tumor rejection and significant tumor growth inhibition as compared to control groups ($p<0.01$)." Uemura et al. concluded that "immunization with Ab2s elicits powerful anti-tumor effects in immunocompetent animals."

Uemura et al., *J. Urol.* 159(5)(Suppl.): Abstract 724 (May 1998), describe MN as an immunotherapeutic target for renal cell carcinoma (RCC). The therapeutic potential of the MN-specific MAb G250 was evaluated in combination with IFN/IL-2/MCSF (interferon, interleukin-2, macrophage colony stimulating factor) and Ab2 (NUH82)-induced mouse serum (Ab3-82). Ab2s are monoclonal anti-idiotype antibodies raised against MAbG250 which have been shown to be useful as tumor vaccines for RCC.

Uemura et al., id. reported that mice with NUR-2 RCC xenografts were treated by peri-tumor injection of MAbG250 and/or cytokines or 0.2 ml of Ab3 sera with/without MCSF. The tumor volume in MAbG250 treated animals was significantly lower than in the controls. IFN or IL-2 treatments was similarly effective, but MCSF resulted in no significant tumor inhibition. The IFN/IL-2/MAbG250 therapy increased significantly the anti-tumor effects as compared to MAbG250 or cytokine monotherapy. Further, Ab3-based (Ab2-induced) immunotherapy resulted in tremendous tumor monotherapy growth inhibition as compared to MAbG250 or the other cytokine combination therapies.

Gene Therapy: Further, a CA IX-specific molecule, such as an anti-CA IX monoclonal antibody, could be coupled to a vector for targeted delivery to CA IX-specific expressing cells for gene therapy (for example, with the wild-type von Hippel-Lindau gene), or for effecting the expression of cytotoxic proteins.

Such methods can be of particular diagnostic and prognostic importance because MN/CA9 is a hypoxia-regulated gene. Hypoxia combined with CA IX overexpression indicates that the mammal from whom the sample was taken is considered to have a poorer prognosis, and decisions on treatment for said mammal are made in view of the presence of said hypoxic conditions. MN/CA IX as a hypoxia marker is useful in general in making therapeutic decisions. For example, a cancer patient whose tumor is known to express MN/CA IX at an abnormally high level would not be a candidate for certain kinds of chemotherapy and radiotherapy, but would be a candidate for hypoxia-selective chemotherapy.

Brown [48] points out at page 157 that "solid tumours are considerably less well oxygenated than normal tissues. This leads to resistance to radiotherapy and anticancer chemotherapy, as well as predisposing to increased tumour metastases." Brown explains how tumor hypoxia can be exploited in cancer treatment. One strategy to exploit tumor hypoxia for cancer treatment proposed by Brown [48] is to use drugs that are toxic only under hypoxic conditions. Exemplary and preferred drugs that could be used under that strategy include tirapazamine and AQ4N, a di-N-oxide analogue of mitozantrome.

A second mode of exploiting hypoxia proposed by Brown [48] is by gene therapy strategies developed to take advantage of the selective induction of HIF-1. Preferably, a gene therapy vector referred to above comprises a MN/CA IX promoter or MN/CA9 promoter fragment comprising the MN/CA IX hypoxia response element (HRE) or a HRE of another gene, and more preferably wherein the CA IX promoter or CA IX promotor fragment comprises more than one HRE, wherein said HRE or HREs is or are either of MN/CA9, and/or of other genes and/or of genetically engineered HRE consensus sequences in a preferred context.

Brown notes that a tumor-specific delivery system can be developed wherein a promoter that is highly responsive to HIF-1 would drive the expression of a conditionally lethal gene under hypoxic but not normoxic conditions. The MN/CA9 promoter is just such a promoter highly responsive to hypoxia, as well as MN/CA9 promoter fragments comprising one or more HREs. "Expression of an enzyme not normally found in the human body could, under the control of a hypoxia-responsive promoter [the MN/CA9 promoter], convert a nontoxic pro-drug into a toxic drug in the tumour." [Brown [48], page 160.] Exemplary is the use of the bacterial cytosine deaminase, which converts the nontoxic 5-fluorocytosine to the anticancer drug 5-fluorouracil (5FU) cited by Brown to Trinh et al. [49].

Ratcliffe et al., U.S. Pat. Nos. 5,942,434 and 6,265,390 explain how anti-cancer drugs become activated under hypoxia, but that the use of a drug activation system, wherein the enzyme that activates the drug is significantly increased under hypoxia, results in much enhanced therapeutic effect.

Computerized MN/CA IX Data Analysis: The correlation of MN/CA9 expression (for example, level and/or extent) and RCC prognosis can be analyzed by any number of methods known to one of skill in the art, for example, by computer program. Such a computer program could comprise algorithms for correlating CA9 expression data derived from a renal cell carcinoma patient with a probable prognosis.

The following examples are for purposes of illustration only and are not meant to limit the invention in any way.

Example 1

The following experiments were designed to investigate whether MN/CA IX could be used as a prognostic marker, as well as a diagnostic marker in RCC, particularly CCC. Nephrectomy specimens from 92 patients were used in this study. Eighty (80) of these were renal cell carcinomas, 10 adenomas and 2 oncocytomas. Of the renal cell carcinomas, 67 were clear cell carcinomas (CCCs). Immunohistochemical analysis using the MN/CA IX-specific monoclonal antibody (M75) was performed on paraffin embedded specimens.

MN/CA IX staining was correlated with tumor stage, grade, lymph node involvement, distant metastasis and cumulative survival time.

MN/CA IX was present in 91.2% of the clear cell carcinomas. Low staining was a poor prognostic factor, and conversely high staining a good prognostic factor. MN expression was found to be the best prognostic factor when compared with T stage and grade. Even in low-grade and stage tumors, the presence of low MN expression correlated with lowered survival times.

The conclusion from the study disclosed herein is that MN is a significant molecular marker in RCCs, particularly CCCs. Decreased MN expression is independently associated with poor survival. MN can be used to predict clinical outcome and identify high-risk patients in need of adjuvant immunotherapy and MN targeted therapies.

Material and Methods

Samples of nephrectomy specimens from 80 cases of RCC, ten renal adenomas and two renal oncocytomas, obtained from the archives of the Pathology Department of çukurova University, were evaluated. All patients had been operated upon in the Urology Department of the same university hospital between 1996 and 2003. Histologic slides of each case were reviewed for diagnostic reassessment. Grading was performed according to Fuhrman nuclear grading system [13].

5-μm thick sections of formalin-fixed, paraffin-embedded tissue samples were deparaffinized and rehydrated through a series of graded alcohols. Antigen retrieval was carried out in citrate buffer (pH 6) for 10 minutes in a microwave oven. For 20-25 minutes, they were rested to cool down to room temperature. After washing slides in PBS for 5 minutes, incubation was done with blocking serum for 10 minutes. Then, a mouse monoclonal antihuman antibody (M75) raised to external domain of MN/CA IX was applied at a concentration of 1/300 for 60 minutes at room temperature [14]. After washing the slides for 5 minutes in PBS, they were incubated at 25° C. in ready-to-use biotinylated Universal Secondary Antibody for 20 minutes (NCL-RTU-D, Novacastra, UK). Afterwards, the slides were washed in PBS for 5 minutes and then incubated at 25° C. in RTU streptavidin/peroxidase complex reagent for 10 minutes. After incubation, slides were washed twice with PBS for 5 minutes once again. The immunperoxidase was visualized with AEC (3-amino-9-ethylcarbazole; DAKO, USA). The sections were counterstained with Mayer's hematoxylin and then coverslipped. An isotypic antibody was used in all staining procedures as a negative control.

The immunohistochemical results were scored semiquantitatively, based upon the percentage of positive cells seen in a total field of a single-section. MN/CA IX antigen is a membrane-associated protein. Therefore, when a cell exhibited sharp and clear membrane staining, it was interpreted as MN/CA IX immunoreactive. Only membrane staining pattern was evaluated using a 0 to 2+ scale (0, completely negative, 1+ focal when $\leq$50% of the cells stained, 2+ diffuse when >50% of the cells stained as described by Liao et al. [12]). The pattern of staining was considered as of low and high expression when the intensity is 0 to 1+ and 2+, respectively. All specimens were examined by two blinded pathologists. Interobserver reliability between the two was 88%.

SPSS ("Statistical Package for the Social Sciences," originally) for Windows version 10.0 was used for statistical analyses. Differences in MN/CA IX staining levels between independent groups were evaluated by Chi square or Fisher's exact test. The Kaplan-Meier method was used to estimate cumulative survival and log-rank test was applied to compare stratified survival functions. The Cox proportional hazards model was used to test the statistical independence and significance of MN/CA IX (age, grade, T stage and MN/CA IX were used in the model as dependent variables). Data were expressed as mean±SD (standard deviation), n (number of cases) and percent (%). A p value less than 0.05 was considered significant.

Results

Of the total 92 specimens, 80 were RCC and of the RCCs 67 clear cell subtype (CCC), 10 papillary and 3 chromophobe. The remaining 12 consisted of 10 adenomas and 2 oncocytomas.

Of the 80 RCCs, 10, 6 of which were CCCs, did not show any staining at all. Therefore MN expression in RCC tumor specimens was 87.5%. Of those which showed staining, 31 stained less than 50% and of those 25 were CCCs. 39 RCCs, 36 CCC and 3 papillary showed more than 50% staining. [Exemplary immunohistochemical staining showed a high pattern of MN/CA IX staining in papillary carcinoma (FIG. 1), and intensive membraneous staining in clear cell carcinoma (FIG. 2).] None of the 10 adenomas showed staining. Of the 2 oncocytomas, 1 did not stain, the other showed less than 50% staining (Table 1).

TABLE 1

Expression of the MN/CA IX in RCC and benign renal lesions

| | | Pattern of Staining | | |
|---|---|---|---|---|
| | n | None | <50% | >50% |
| Renal Cell Carcinoma | | | | |
| Clear Cell Carcinoma | 67 | 6 | 25 | 36 |
| Papillary Cell Carcinoma | 10 | 2 | 5 | 3 |
| Chromophobe Cell | 3 | 2 | 1 | — |
| Adenoma | 10 | 10 | — | — |
| Oncocytoma | 2 | 1 | 1 | — |

Overall, 67 RCC patients with clear cell type were included in the analysis. The patients' age at the time of surgery ranged from 18 to 81 years (mean of 54.8±11.6 years). The male/female ratio was 1.9:1 with 44 male patients (65.7%) and 23 female patients (34.3%). Radical nephrectomy was performed on 62 patients (92.5%) and partial nephrectomy on 5 (7.5%). As for pathologic stage, 22 cases were stage I, 31 stage II, 8 stage III and 6 were stage IV. As for pathological grade, there were 24 grade 1 (35.8%), 20 grade 2 (29.9%), 16 grade 3 (23.9%) and 7 grade 4 cases (10.4%). Table 2 lists patient and tumor characteristics.

TABLE 2

Characteristics of RCC patients

| Patient Characteristics | Patient Data n = 67 (%) |
|---|---|
| Sex | |
| Male | 44 (65.7) |
| Female | 23 (34.3) |
| Side | |
| Right | 31 (46.3) |
| Left | 36 (53.7) |
| Age (years) | |
| Mean ± SD | 54.8 ± 11.6 |
| Median | 54.0 |
| Min-Max | 18-81 |

TABLE 2-continued

Characteristics of RCC patients

| Patient Characteristics | Patient Data n = 67 (%) |
|---|---|
| Operation | |
| Partial nephrectomy | 5 (7.5) |
| Radical nephrectomy | 62 (92.5) |
| T Stage | |
| 1 | 22 (32.8) |
| 2 | 31 (46.2) |
| 3 | 8 (11.9) |
| 4 | 6 (8.9) |
| Grade | |
| 1 | 24 (35.8) |
| 2 | 20 (29.9) |
| 3 | 16 (23.9) |
| 4 | 7 (10.4) |
| Metastasis | |
| Yes | 4 (6.0%) |
| No | 63 (94.0%) |

The relation of staining pattern in CCC with pathologic T and N stage, M stage and grade of the tumor were evaluated, and the results are given in Table 3. Low stage T tumors showed high CA IX staining in 66% of the cases, whereas high stage T tumors showed mostly low CA IX staining (92.9%). When there was no lymph node involvement, there was a high pattern of staining in 57.1% of the cases; whereas with lymph node involvement, a low pattern of CA IX staining was seen in all (100%) cases. Of the total, 63 patients had no distant metastasis; 36 (57.1%) of them showed a high pattern of CA IX staining. All of the 4 (100%) patients with distant metastasis had a low pattern of CA IX staining. Low grade (1 or 2) tumors had mostly high CA IX staining (71.1%); whereas high grade (3 or 4) tumors mostly had low CA IX staining (81.8%) (Table 3).

TABLE 3

Relation of staining pattern with pathologic stage T and N, metastasis and grade

| | Pattern of staining | | |
|---|---|---|---|
| | low (n = 31) n (%) | high (n = 36) n (%) | p value |
| T-Stage | | | |
| Low (1 or 2) | 18 (34.0) | 35 (66) | 0.000 |
| High (3 or 4) | 13 (92.9) | 1 (7.1) | |
| Nodes | | | |
| No | 27 (42.9) | 36 (57.1) | 0.04 |
| Yes | 4 (100.0) | — | |
| Metastasis | | | |
| No | 27 (42.9) | 36 (57.1) | 0.04 |
| Yes | 4 (100.0) | — | |
| Grade | | | |
| Low (1 or 2) | 13 (28.9) | 32 (71.1) | 0.000 |
| High (3 or 4) | 18 (81.8) | 4 (18.2) | |

Of the CCC patients, 6 were lost to follow-up. Mean and median cumulative survival of the 61 remaining patients according to T stage, grade and CA IX expression is given in detail in Table 4 and FIGS. 3a, b, c, 4 and 5. In the group with high CA IX expression, mean cumulative survival was 64.1 months. When grade was considered, in the low grade group mean cumulative survival was 53.5 months; however, when there was low CA IX expression in the low-grade tumors, survival dropped to 28.7 months. Similarly, the cumulative survival rate of 49.4 months in the low T stage tumors dropped to 28.7 months when such low grade tumors showed a low level of CA IX staining. Cumulative survival correlated with the level of CA IX staining (p=0.000) with grade (p=0.006) and T stage (p=0.02) of the tumor.

TABLE 4

Mean and median cumulative survival (months) for patients (n = 61) according to T Stage, Grade and MN/CA IX expression

| | Mean (median) | dead/total | p value |
|---|---|---|---|
| Grade | | | |
| Low (1 or 2) | 53.5 (61) | 20/39 | 0.006 |
| High (3 or 4) | 22.6 (16) | 17/22 | |
| T stage | | | |
| Low (1 or 2) | 49.4 (39) | 26/47 | 0.02 |
| High (3 or 4) | 19.3 (12) | 11/14 | |
| CA IX | | | |
| Low (<%50) | 23.4 (12) | 24/29 | 0.000 |
| High (>%50) | 64.1 (64) | 13/32 | |
| Grade (Gr) and CA IX | | | |
| Low Gr-Low CA IX | 28.7 (11) | 8/11 | 0.0003 |
| Low Gr-High CA IX | 61.7 (67) | 12/28 | |
| High Gr-Low CA IX | 15.5 (14) | 16/18 | |
| High Gr-High CA IX | 61.0 (40) | 1/4 | |
| T stage (Stg) and CA IX | | | |
| Low T Stg-Low CA IX | 19.7 (11) | 14/16 | 0.0001 |
| Low T Stg-High CA IX | 64.3 (64) | 12/31 | |
| High T Stg-Low CA IX | 20.2 (16) | 10/13 | |
| High T Stg-High CA IX | 8 (—) | 1/1 | |

Conversely, the high tumor grade patients had a survival rate of 22.6 months, but when CA IX staining was high in the high grade tumors, survival jumped up to 61 months. A similar conclusion could not be arrived at in the high stage-high CA IX expression group because there was only one patient, and he survived for 8 months.

The Cox proportional hazards model results are shown in Table 5. The results show that CA IX is an independent and significant factor related with survival rate in RCC patients.

TABLE 5

Results of Cox regression model

| Variables in equation | OR | 95% CI for OR (Lower-Upper) | P value |
|---|---|---|---|
| Age | 0.9 | (0.9-1.0) | 0.270 |
| Grade | 1.5 | (0.7-3.3) | 0.304 |
| T Stage | 1.3 | (0.6-3.1) | 0.529 |
| CA IX | 3.9 | (1.7-9.0) | 0.001 |

Discussion

In this study of 80 RCCs, CA IX staining was 87.5%, which is consistent with previous reports [7]. In the CCC group, the staining rate was 91%, which suggests CA IX to be a strong biomarker especially for the clear cell subtype of RCC. Murakami et. al. [10] found CA IX expression in CCC to be 92%; that rate was reported by Bui et al. [15] to be 94%.

As for its prognostic value, a low level of CA IX staining correlated with worse outcome. High T stage tumors had low CA IX expression (92.9%). Even though only four of the cases had lymph node involvement, all of those cases had a low level of CA IX staining. As for distant metastasis, all had low CA IX expression again, whereas only 42.9% of cases with no metastasis stained in the same pattern. Again with high tumor grade, there was a high rate of low CA IX expression (81.8%). When the cumulative survival rate was correlated with the tumor grade, stage and CA IX expression, CA IX expression was at least as good a factor effecting survival rate as T-stage and tumor grade. Since the number of patients was insufficient, survival due to N and M stages could not be estimated.

The overall survival rate in the subject study group is lower than that reported in the literature [1]. That again may be due to the limited number as well as possibly the socioeconomic status of the patients.

In all of the low CA IX, high stage and high tumor grade groups, survival rates were similar (19.3, 22.6, 23.6 months, respectively). However, lowest survival rates were seen when there is low CA IX in high grade (15.5 months) and low CA IX in high stage (20.3 months) tumors. It is therefore crucial to predict those subsets of patients in order to establish more aggressive therapy regimens.

RCC has been shown to respond to biological immunotherapy. Responses to systemic cytokine therapy in metastatic RCC are promising, although the overall results are still inadequate. Careful patient selection and stratification to various adjuvant immunotherapies may delineate those patients most likely to respond to treatment.

In conclusion, MN/CA IX is shown herein to be a significant and promising molecular marker in the prognosis of RCCs/CCCs. Decreased MN/CA IX expression is independently associated with poor survival. MN/CA IX can be used to predict clinical outcome and tumor behavior. MN/CA IX can identify high-risk patients who could benefit from adjuvant immunotherapy, and MN/CA IX targeted therapies among other therapies, as exemplified by those described above.

Budapest Treaty Deposits

The materials listed below were deposited with the American Type Culture Collection (ATCC) now at 10810 University Blvd., Manassus, Va. 20110-2209 (USA). The deposits were made under the provisions of the Budapest Treaty on the International Recognition of Deposited Microorganisms for the Purposes of Patent Procedure and Regulations thereunder (Budapest Treaty). Maintenance of a viable culture is assured for thirty years from the date of deposit. The hybridomas and plasmids will be made available by the ATCC under the terms of the Budapest Treaty, and subject to an agreement between the Applicants and the ATCC which assures unrestricted availability of the deposited hybridomas and plasmids to the public upon the granting of patent from the instant application. Availability of the deposited strain is not to be construed as a license to practice the invention in contravention of the rights granted under the authority of any Government in accordance with its patent laws.

|  | Deposit Date | ATCC # |
|---|---|---|
| Hybridoma |  |  |
| VU-M75 | Sep. 17, 1992 | HB 11128 |
| MN 12.2.2 | Jun. 9, 1994 | HB 11647 |
| Plasmid |  |  |
| A4a | Jun. 6, 1995 | 97199 |
| XE1 | Jun. 6, 1995 | 97200 |
| XE3 | Jun. 6, 1995 | 97198 |

Similarly, the hybridoma cell line V/10-VU which produces the V/10 monoclonal antibodies was deposited on Feb. 19, 2003 under the Budapest Treaty at the International Depository Authority (IDA) of the Belgian Coordinated Collections of Microorganisms (BCCM) at the Laboratorium voor Moleculaire Biologie-Plasmidencollectie (LMBP) at the Universeit Gent, K. L. Ledeganckstraat 35, B-9000 Gent, Belgium [BCCM/LMBP] under the Accession No. LMBP 6009CB.

The description of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to explain the principles of the invention and its practical application to enable thereby others skilled in the art to utilize the invention in various embodiments and with various modifications as are suited to the particular use contemplated.

All references cited herein are hereby incorporated by reference.

The invention claimed is:

1. A method which is prognostic for nonmetastatic renal cell carcinoma afflicting a vertebrate, wherein the tumor T-stage is 2 or lower, said method comprising:
   (a) detecting the presence or absence of MN/CA9 gene expression product in a sample comprising neoplastic cells taken from said vertebrate,
   (b) if MN/CA9 gene expression product is present in said sample, quantitating the level and/or extent of said MN/CA9 gene expression product relative to the number of cells in said sample, and
   (c) determining that said vertebrate has a poorer prognosis if the level and/or extent of MN/CA9 gene expression product of steps (a) and (b) indicates that 50% or fewer of cells in said sample express MN/CA9 gene expression product;
   wherein said MN/CA9 gene expression product is encoded by a nucleotide sequence selected from the group consisting of:
   (1) SEQ ID NO: 1's coding region;
   (2) nucleotide sequences that hybridize under stringent hybridization conditions of 50% formamide at 42 degree C. to complement of SEQ ID NO: 1's coding region; and
   (3) nucleotide sequences that differ from SEQ ID NO: 1's coding region or from the nucleotide sequences of (2) in codon sequence due to the degeneracy of the genetic code;
   and wherein if said MN/CA9 gene expression product is MN/CA IX protein or MN/CA IX polypeptide, said MN/CA IX protein or said MN/CA IX polypeptide is specifically bound by the M75 monoclonal antibody that is secreted from the hybridoma VU-M75 which has Accession No. ATCC HB 11128.

2. The method of claim 1, wherein said renal cell carcinoma in said vertebrate is selected from the group consisting of renal clear cell carcinoma, papillary cell carcinoma and chromophobe carcinoma.

3. The method of claim 1 wherein said renal cell carcinoma is renal clear cell carcinoma.

4. The method of claim 1, wherein detecting step (a) comprises immunohistochemical staining with MN/CA IX-specific antibody to detect the presence or absence of MN/CA IX protein in the sample, and wherein quantitating step (b) comprises determining the percentage of MN/CA IX immunoreactive cells, wherein if 50% or fewer of cells in said sample are immunoreactive, concluding in step (c) that said vertebrate has a poorer prognosis than if more than 50% of cells in said sample are immunoreactive.

5. The method of claim 1, wherein detecting step (a) comprises immunohistochemical staining with MN/CA IX-specific antibody to detect the presence or absence of MN/CA IX protein in the sample, and wherein quantitating step (b) comprises determining a MN/CA IX immunoreactivity score of cells in said sample, comprising determining the percentage of immunoreactive cells with cell membrane staining, wherein the percentage of immunoreactive cells is assigned an immunoreactivity score with
   a value of 0 if no immunoreactive cells,
   a value of 1 if 50% or less immunoreactive cells, or
   a value of 2 if more than 50% immunoreactive cells;
   and
   wherein if the immunoreactivity score of the sample is 1 or less, concluding in step (c) that said vertebrate has a poorer prognosis than if said immunoreactivity score is 2.

6. The method of claim 1, wherein a poorer prognosis is measured in terms of shortened cumulative survival, increased risk of recurrence of said renal cell carcinoma and/or increased risk of metastasis.

7. The method of claim 1, wherein said sample is a formalin-fixed, paraffin-embedded tissue sample.

8. The method of claim 1, wherein said MN/CA9 gene expression product comprises an MN/CA IX protein or MN/CA IX polypeptide.

9. The method of claim 1, wherein said MN/CA9 gene expression product comprises a mRNA encoding an MN/CA IX protein or MN/CA IX polypeptide, or a cDNA complementary to said mRNA.

10. The method according to claim 1, wherein said detecting step (a) comprises immunologically detecting with an assay selected from the group consisting of Western blots, enzyme-inked immunosorbent assays, radioimmunoassays, competition immunoassays, dual antibody sandwich assays, immunohistochemical staining assays, agglutination assays, and fluorescent immunoassays.

11. The method of claim 1, wherein said detecting step (a) is by in situ hybridization, Northern blotting, PCR, RT-PCR, real-time PCR, or by quantitative real-time RT-PCR.

12. The method according to claim 1, wherein said detecting step (a) comprises immunologically detecting with the monoclonal antibody secreted by the hybridoma VU-M75 which has Accession No. ATCC HB 11128.

13. The method according to claim 1, wherein said detecting step (a) is by immunohistochemical staining, and wherein said quantitating step (b) comprises determining the percentage of MN/CA IX immunoreactive cells.

14. The method according to claim 1, wherein said detecting step (a) is by immunohistochemical staining, and wherein said quantitating step (b) comprises determining the percentage and/or the intensity and/or extent of immunostaining of immunoreactive cells.

15. The method of claim 1, wherein said vertebrate is a mammal.

16. The method of claim 15, wherein said mammal is a human.

17. The method of claim 1, wherein said prognostic method is used as an aid in the selection of treatment for said renal cell carcinoma afflicting said vertebrate.

18. The method of claim 17, wherein if quantitating step (b) indicates that more than 50% of cells in said sample express MN/CA9 gene expression product, said vertebrate is identified as a candidate for MN/CA9-directed therapy.

19. The method of claim 1, wherein even if the tumor T-stage is 2 or lower and the Fuhrman grade is 2 or lower in said vertebrate, if 50% or less of cells in said sample express MN/CA9 gene expression product, said vertebrate has a worse prognosis than if more than 50% of cells in said sample express MN/CA9 gene expression product.

* * * * *